(12) United States Patent
Allen et al.

(10) Patent No.: US 9,271,814 B2
(45) Date of Patent: Mar. 1, 2016

(54) FLOSSING DEVICE

(71) Applicant: ORALWISE, INC, Dallas, TX (US)

(72) Inventors: Keith Bornstein Allen, Woodland Hills, CA (US); Dan Voetmann, Mountlake Terrace, WA (US)

(73) Assignee: OralWise, INC., Dallas, TX (US)

( * ) Notice: Subject to any disclaimer, the term of this patent is extended or adjusted under 35 U.S.C. 154(b) by 0 days.

(21) Appl. No.: 14/062,314

(22) Filed: Oct. 24, 2013

(65) Prior Publication Data

US 2014/0048096 A1 Feb. 20, 2014

Related U.S. Application Data

(63) Continuation-in-part of application No. 13/169,962, filed on Jun. 27, 2011, now Pat. No. 8,596,286.

(51) Int. Cl.
| | | |
|---|---|---|
| *A45D 24/10* | (2006.01) | |
| *A45D 7/00* | (2006.01) | |
| *A61C 15/00* | (2006.01) | |
| *A61C 15/04* | (2006.01) | |

(52) U.S. Cl.
CPC ......... *A61C 15/046* (2013.01); *Y10T 29/49838* (2015.01)

(58) Field of Classification Search
CPC ...... A61C 15/04; A61C 15/046; A61C 15/00; A61C 15/02; A61C 15/043; A61C 15/045; A61C 15/048; A61C 15/047; A61C 15/041; A61C 15/042; Y10T 29/49838
USPC .......... 132/321–329, 309, 200; 433/146, 147, 433/216, 141, 134, 29; 84/422.4; D28/65, D28/66, 68; 206/63.3, 63.5
See application file for complete search history.

(56) References Cited

U.S. PATENT DOCUMENTS

| | | | | |
|---|---|---|---|---|
| 1,815,408 | A * | 7/1931 | Jordan | 132/323 |
| 2,180,522 | A * | 11/1939 | Isabelle | 132/323 |
| 3,393,687 | A * | 7/1968 | Whitman | 132/323 |
| 3,799,177 | A | 3/1974 | Bragg | |
| 4,304,246 | A | 12/1981 | Yafai | |
| 4,403,625 | A * | 9/1983 | Sanders et al. | 132/323 |
| 4,519,408 | A | 5/1985 | Charatan | |
| 4,633,892 | A * | 1/1987 | Charatan | 132/321 |
| 4,655,233 | A | 4/1987 | Laughlin | |
| 4,926,820 | A * | 5/1990 | Wearn | 132/323 |
| 4,941,488 | A | 7/1990 | Marxer et al. | |
| 4,982,752 | A | 1/1991 | Rodriguez | |
| 4,986,289 | A * | 1/1991 | McWhorter | 132/323 |

(Continued)

FOREIGN PATENT DOCUMENTS

WO  WO8807354  10/1988

*Primary Examiner* — Vanitha Elgart
(74) *Attorney, Agent, or Firm* — JP Webb; Jason P. Webb; Danny Y. H. Cheng

(57) ABSTRACT

A flossing device and a method of manufacture thereof, consisting of a first elongated member and a second elongated member that is removably coupled to the first elongated member along an interior side of a top region of the first elongated member. The flossing device includes a floss member coupled to the second elongated member and extending through an aperture of the first elongated member. The floss member includes a first enlarged stop member at an end distal from the second elongated member and sized to fit within a countersunk enlarged channel but not fit through a narrow channel in communication with the enlarged channel.

18 Claims, 18 Drawing Sheets

(56) References Cited

U.S. PATENT DOCUMENTS

| | | | |
|---|---|---|---|
| 5,067,503 A | 11/1991 | Stile | |
| 5,123,432 A | 6/1992 | Wyss | |
| 5,127,415 A | 7/1992 | Preciutti | |
| 5,199,452 A * | 4/1993 | Cheng | 132/325 |
| 5,222,510 A | 6/1993 | Zuehlsdorf | |
| 5,224,501 A | 7/1993 | McKenzie | |
| 5,406,965 A * | 4/1995 | Levine | 132/323 |
| D358,001 S * | 5/1995 | Ramsey | D28/68 |
| 5,435,330 A | 7/1995 | Dix | |
| 5,469,874 A | 11/1995 | Meyer et al. | |
| 5,477,871 A * | 12/1995 | Sanchez, Jr. | 132/323 |
| 5,503,168 A * | 4/1996 | Wang | 132/324 |
| 5,564,446 A | 10/1996 | Wiltshire | |
| 5,570,710 A * | 11/1996 | Wei et al. | 132/323 |
| 5,680,875 A * | 10/1997 | Winters | 132/324 |
| 5,692,532 A * | 12/1997 | Gabrovsek | 132/325 |
| 5,765,577 A * | 6/1998 | Wei et al. | 132/323 |
| 5,860,435 A | 1/1999 | Hippensteel | |
| 5,911,229 A * | 6/1999 | Chodorow | 132/323 |
| 5,915,392 A | 6/1999 | Isaac | |
| 6,003,525 A * | 12/1999 | Katz | 132/321 |
| 6,019,109 A | 2/2000 | Moore | |
| 6,065,480 A | 5/2000 | Mader | |
| 6,131,586 A * | 10/2000 | Flanagan | 132/325 |
| 6,161,556 A | 12/2000 | Gutierrez | |
| 6,220,257 B1 | 4/2001 | Meyer et al. | |
| 6,234,182 B1 * | 5/2001 | Berglund | 132/323 |
| 6,895,977 B2 | 5/2005 | Guo | |
| 7,819,126 B2 * | 10/2010 | Bush | 132/323 |
| 2004/0134510 A1 | 7/2004 | van Vilsteren et al. | |
| 2004/0154636 A1 * | 8/2004 | Paz-Soldan | 132/323 |
| 2004/0250834 A1 * | 12/2004 | Bowsher | 132/323 |
| 2008/0178904 A1 * | 7/2008 | Peters | 132/323 |
| 2009/0020134 A1 * | 1/2009 | Tomsic et al. | 132/327 |
| 2010/0018547 A1 | 1/2010 | Roemuss | |
| 2011/0155168 A1 * | 6/2011 | Chung | 132/327 |
| 2012/0234350 A1 * | 9/2012 | Mowell et al. | 132/323 |
| 2013/0160790 A1 * | 6/2013 | Yap | 132/324 |

* cited by examiner

FLOSSING DEVICE

CROSS-REFERENCE TO RELATED APPLICATIONS

This application is a Continuation In Part application of, under 35 U.S.C. §121, and claims priority to, under 35 U.S.C. §121, U.S. Non-Provisional application Ser. No. 13/169,962, entitled Flossing Device, by Keith Allen Bornstein, filed on Jun. 27, 2011, which is incorporated by reference herein for its supporting teachings.

BACKGROUND OF THE INVENTION

1. Field of the Invention

The present invention relates to dental tools, specifically flossing devices.

2. Description of the Related Art

Dental floss is generally a bundle of thin nylon filaments or a plastic (Teflon or polyethylene) ribbon used to remove food and dental plaque from teeth. The floss is gently inserted between the teeth and scraped along the teeth sides, especially close to the gums. Dental floss may be flavored or unflavored, and waxed or unwaxed. An alternative tool to achieve a similar effect is the interdental brush.

Dental floss is commonly supplied in plastic dispensers that contain 10 to 50 meters of floss. After pulling out the desired amount, the floss is pulled against a small protected blade in the dispenser to sever it. Dental floss is held between the fingers. The floss is guided between each tooth and under the gumline to remove particles of food stuck between teeth and dento-bacterial plaque that adhere to such dental surfaces. Ideally using a C-shape, the floss is curved around a tooth and placed under the gumline, and then moved away from the gumline, the floss scrapes the side of each tooth, and can also clean the front or back of the tooth. Gently moving the floss from below the gumline to away from the gumline removes dento-bacterial plaque attached to teeth surfaces above and below the gumline. A clean section of floss can be used to clean each tooth to avoid transmitting plaque bacteria from one tooth to another.

There are many different kinds of dental floss commonly available. The most important variable is thickness. If the floss is too thick for the space between a pair of teeth then it will be difficult or impossible to get the floss down between the teeth. On the other hand, if the floss is too thin, it may be too weak and break. Different floss will suit different mouths, and even different parts of one mouth. This is because some teeth have a smaller gap between them than others. Its possible that thicker floss does a better job of scraping bacterial plaque off teeth, given that there is space enough between the teeth to use it. When a piece of hard food is tightly wedged between the teeth, one may need to switch to thinner floss, because thick floss cannot get past the food. It is possible to split some kinds of dental floss lengthwise generating a pair of thinner pieces that are much weaker but sometimes usable. This is possible because some kinds of dental floss are made of many very thin strands that are not woven together but rather run more or less in parallel. This can also be useful if the dental floss you have is too thick for you, for any other reason, and you do not have access to any other, for example when travelling in a foreign country.

Specialized plastic wands, or floss picks, have been produced to hold the floss. These may be attached to or separate from a floss dispenser. While wands do not pinch fingers like regular floss can, using a wand may be awkward and can also make it difficult to floss at all the angles possible with regular floss. These types of flossers also run the risk of missing the area under the gum line that needs to be flossed. On the other hand, the enhanced reach of a wand can make flossing the back teeth easier.

Ergonomic flossers with improved handle for better grip and swiveling floss heads allow easy access to any pair of teeth in the mouth, to the front teeth as well as to the rear teeth. Their floss heads also feature a lateral flexibility that enables improved control for the dental floss to hug the sides of the teeth and clean under the gum line without the danger of hurting the gums. Occasional flossing and/or improper flossing can typically lead to bleeding gums. The main cause of the bleeding is inflammation of the gingival tissue due to gingivitis.

Some improvements have been made in the field. Examples of references related to the present invention are described below in their own words, and the supporting teachings of each reference are incorporated by reference herein:

U.S. Pat. No. 6,895,977, issued to Guo, discloses a dental flossing tool for dispensing floss for cleaning the user's teeth. A handle body surrounds a cavity and has a lead riser from which dental floss is dispensed for use. The floss is wound upon a spool that rotates inside the cavity. Floss is paid out from the spool and emerges from a hole in the tip of the lead riser. A button or handle is slidably mounted upon the apparatus for controlling the longitudinal movement of a retainer within the cavity of the apparatus. By sliding the button handle forward and backward, the user can disengage and engage the retainer with a baffle attached to the spool inside the body of the apparatus. When the retainer is in contact with the baffle, the spool is prevented from rotating, thereby stopping any further floss from being dispensed. When the retainer is disengaged out of contact with the baffle, the spool is free to rotate to pay out floss. A removable protector is provided for covering the lead riser and a floss cutter blade attached to the exterior of the apparatus. The protector can be removed to the back end of the apparatus to extend its graspable portion for easier handling.

U.S. Pat. No. 6,019,109, issued to Moore, discloses a dental flossing tool and method for flossing of the teeth using that tool is provided. The tool includes two elongated, rod-shaped handle elements and a length of dental floss that is removably secured at its opposite ends to respective ones of the handle elements at their terminal ends. Each handle element is provided with a bulb at the terminal end to which the floss is attached with the bulbs being larger in transverse cross-section relative to the longitudinal axis of its handle element than is the adjacent portion of the handle element. This results in a depressed annular region in which floss is wound and functions to retain the floss on a handle element. Each handle element includes a hand-grip section disposed in remote relationship to the terminal end provided with a bulb enabling a user to grip the element in a respective hand for support thereof and independent manipulation in effecting a flossing operation. The user holds the handle elements in separated relationship to maintain the floss extending between the terminal ends taut as an operative flossing section while inserting it between a pair of adjacent teeth and moving it to effect removal of debris. At intermittent intervals the user revolves the handle elements to concurrently unreel a length of floss from one and reel a length onto the other thereby placing an unused section of floss in an operative position and placing the previously used section on a handle element for storage until being discarded upon termination of a flossing operation.

U.S. Pat. No. 5,915,392, issued to Isaac, discloses a toothpick apparatus of the present invention consists of an elongated cylindrical device 13 having a thicker middle portion 17 tapering away from the middle toward opposing ends or points 19. The toothpick has a perforated area or break point near its middle 17 whereby when the toothpick is broken a useable length of dental floss 23 is exposed. The dental floss 23 is contained within layers of thin wood 21 which are rolled in order to form the toothpick. Additional embodiments of the present invention are also described.

U.S. Pat. No. 5,224,501, issued to McKenzie, discloses an improved device for holding and manipulating dental floss for the removal of food particles, tartar and plaque from the teeth is described in which a loop of dental floss is connected between a pair of separate handles; the loop of dental floss being long enough to permit lateral motion across the tooth surface. The devices are either disposable or sterilizable for reuse.

U.S. Pat. No. 5,123,432, issued to Wyss, discloses a double-ended hand held flossing tool with stressing means is provided which uses a loop of floss made integral with the frame members of the tool, and provides stressing action through fingertip manipulation of the members. The loop is integral and structural to the tool, thus my tool design gains the advantage of stability by virtue of two members being integral with a floss loop molded directly into the construction of the frame members of the tool.

The inventions heretofore known suffer from a number of disadvantages which include being limited in application, being too large, not being disposable, being limited in use, being difficult to use, being difficult to re-use, being expensive, being difficult to manufacture, failing to adequately clean between teeth, damaging gums, not clearly communicating to a user when a device has already been used, requiring significant manual dexterity to operate, and the like.

What is needed is a flossing device that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available flossing devices. Accordingly, the present invention has been developed to provide a flossing device that may be quickly and easily be ready for use.

According to one embodiment of the invention, there is a flossing device that may consist of a first elongated member. The first elongated member may include a top region that may have an exterior side and an interior side opposite each other. The exterior side may be on an outside surface of the first elongated member. The first elongated member may include an aperture through the top region between the exterior side and the interior side. The aperture may be countersunk, thereby having a narrow channel that may be coupled to an enlarged channel. The enlarged channel may be on the exterior side of the first elongated member.

The flossing device may include a second elongated member that may be removably coupled to the first elongated member along the interior side of the top region of the first elongated member. The flossing device may include a floss member that may be coupled to the second elongated member and may be extending through the aperture of the first elongated member. The floss member may include a first enlarged stop member at an end distal from the second elongated member and may be sized to fit within the enlarged channel but may not fit through the narrow channel.

The second elongated member may include a top region that may have an exterior side and an interior side opposite each other. The second elongated member may include an aperture through the top region between the exterior side and the interior side. The aperture may be countersunk, thereby having a narrow channel that may be coupled to an enlarged channel. The enlarged channel may be on the exterior side of the first elongated member, and wherein the floss member may include a second enlarged stop member distal the first stop member and may be sized to fit within the enlarged channel of the second elongated member but may not fit through the narrow channel of the second elongated member.

The first enlarged stop member may be larger in cross-sectional area than the enlarged channel, that may consist of a deformable material, and may be sized sufficiently small to be wedged into the enlarged channel when pulled thereagainst. The first enlarged stop member may consist of knotted floss. The top regions of each of the first and second elongated members may be rectangular columns. The first and second elongated members may be removably coupled together by a breakaway bridge of material therebetween that may be at a bottom region of the elongated members. The enlarged channel may transition into the narrow channel in a single stepped transition without a gradual decrease in channel width. The enlarged channel may transition into the narrow channel by a gradual decrease in channel width.

The first and second elongated members may be formed from a single unitary piece of material.

According to one embodiment of the invention, there is a flossing device that may include a pair of flossing sticks that may be coupled together by a bridge of breakaway material at a top region of the pair of flossing sticks. The pair of flossing sticks may include an aperture through the top region of a first floss stick of the pair of floss sticks. The aperture may extend from an exterior surface of the first floss stick to a second floss stick of the pair of floss sticks. The aperture may be countersunk at the exterior surface and the exterior surface being opposite the bridge of breakaway material. The pair of flossing sticks may include a floss string that may be coupled to the second floss stick, that may be disposed through the aperture and may be extending out of the exterior surface of the pair of floss sticks. The floss string may include a stop member that may be sized to mate with the countersunk aperture when pulled thereagainst but to not pass through aperture, thereby coupling the pair of sticks together with floss therebetween when the pair of flossing sticks are separated at the bridge of breakaway material.

The second floss stick may include a countersunk aperture that may be in communication with and opposite to the aperture of the first floss stick. The pair of flossing sticks and bridge may be a singular formed material. The stop member may be elastic and may be sized to wedge within the countersunk aperture such that, when tension is released from the pair of floss sticks when they are separated after having been pulled apart and the stop member so wedged, the stop member may remain wedged within the countersunk aperture. The floss string may include a second stop member that may extend out of the countersunk aperture of the second floss stick.

According to one embodiment of the invention, there is a method of manufacturing a flossing device that may include the step of providing a pair of joined sticks that may include a first stick and a second stick. The sticks may be joined side by side at their feet by a breakable bridge therebetween. The method may include the step of drilling a countersunk hole through both of the heads of the joined sticks, the countersunk region may be at an exterior surface of the first stick. The method may include threading a floss string through the countersunk hole. The method may include the step of coupling the floss string to the second stick. The method may further include the step of providing a stop member at an end of the floss string. The stop member may be configured to mate with the countersunk hole when pulled thereagainst but not to pass therethrough.

The method of manufacturing a flossing device may include the step of drilling a second countersunk region in the second stick opposite the first stick. The method may include the step of coupling the floss string to the second stick includes providing a second stop member at an opposite end of the floss string. The stop member may consist essentially of knotting the floss string. The joined sticks may be shaped like chopsticks. The step of providing a pair of joined sticks may include forming the pair of joined sticks from a single material.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

Figure 1:
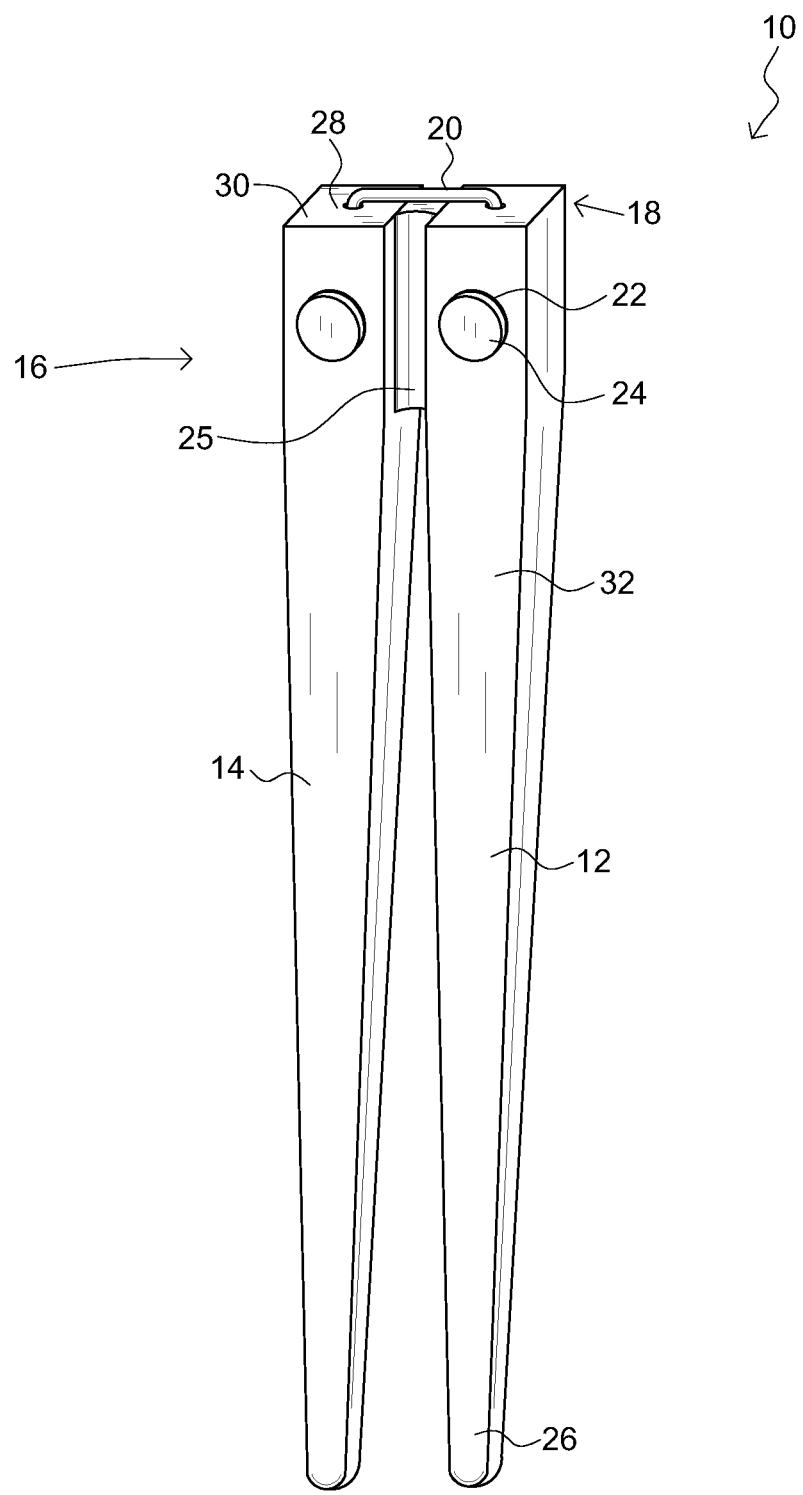
FIG. 1 is a perspective view of a flossing device in a first mode, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 is a perspective view of a flossing device in a first mode, according to one embodiment of the invention. There is shown a first elongated member 12 and a second elongated member 14 of a flossing device 10 in a first mode 16, wherein the first and second elongated members are coupled one to the other by a connector (herein also called breakaway bridge or breakable bridge) 25 and by a floss string 20. The illustrated flossing device 10 is similar to a pair of disposable chopsticks wherein the top ends are coupled by extendable floss.

The flossing device 10 includes a first elongated member 12 and a second elongated member 14. The illustrated flossing device 10 is in a first mode 16, wherein the first elongated member 12 and the second elongated member 14 are coupled along a top end (herein also called a head or head region) 18 by a connector 25 and an extendable floss string 20. The illustrated connector is a connecting strip of material that is shaped, sized or otherwise configured to break/separate/disengage/etc. when subject to an appropriate force in a manner that maintains the integrity of the elongated members while permitting the elongated members to be distanced one from the other. In one embodiment, a connector is a narrow neck such as commonly used with disposable wooden chopsticks. In one embodiment, a connector is an adhesive layer, a brittle material, paired snaps, hook and loop connectors, and/or other connectors.

The illustrated first elongated member 12 and the second elongated member 14, when in the first mode 16, are positioned parallel to each other. The illustrated first elongated member 12 and the illustrated second elongated member 14 each include a tapered end 26, opposite of the top end 18, configured to provide gripping handles to a user. The illustrated elongated members 12 and 14 are substantially rigid members formed of a material suitable for placement in the mouth of a user and suitable for grasping in the hands of a user. While varieties of wood and plastic are expected to be suitable materials, it is understood that other materials may also be suitable, including but not limited to composite materials. Elongated members (sticks, handles, grips, manipulators, arms, etc.) may include features and/or structures that may facilitate use, such as but not limited to rounded top ends, gripping ridges, curved or angled portions, and the like and combinations thereof.

The illustrated flossing device 10 includes a floss string 20 disposed within each of the first elongated member 12 and the second elongated member 14 and extends out a top aperture 28 disposed on a top surface 30 of each of the elongated members 12, 14. It is understood that floss string may extend out of a top end through a surface other than a top surface of the top end. Ross string may include filaments, ribbons, woven fibers, and the like or combinations thereof. It may be augmented by wax, flavorings, coatings, and the like and combinations thereof.

The illustrated flossing device 10 includes a seal 24 and an aperture 22 disposed on a side surface 32 of the first elongated member 12 and of the second elongated member 14. The seal 24 and the aperture 22 are disposed adjacent a channel, disposed within each of the first elongated member 12 and of the second elongated member 14. The aperture 22 is in communication with the channel, thereby facilitating manufacture of the flossing device by providing access to a bottom portion of the channel. The seal 24 and the aperture 22 are configured to provide access to the channel of each of the first elongated member 12 and the second elongated member 14. The seal 24 is configured to seal the aperture 22 and secure the contents of the channel therein. In one non-limiting example, the seal is a hardened polymer that has been disposed within the aperture in a fluid form and then caused to be hardened therein. In another non-limiting example, the seal includes an elastic material shaped and sized to friction-fit within the aperture. In another non-limiting example, the seal snaps into place. In another non-limiting example, the seal is threaded to match threads of the aperture and screws into the aperture. The floss string 20 is contained within the channel of each of the first elongated member 12 and the second elongated member 14.

Figure 2:
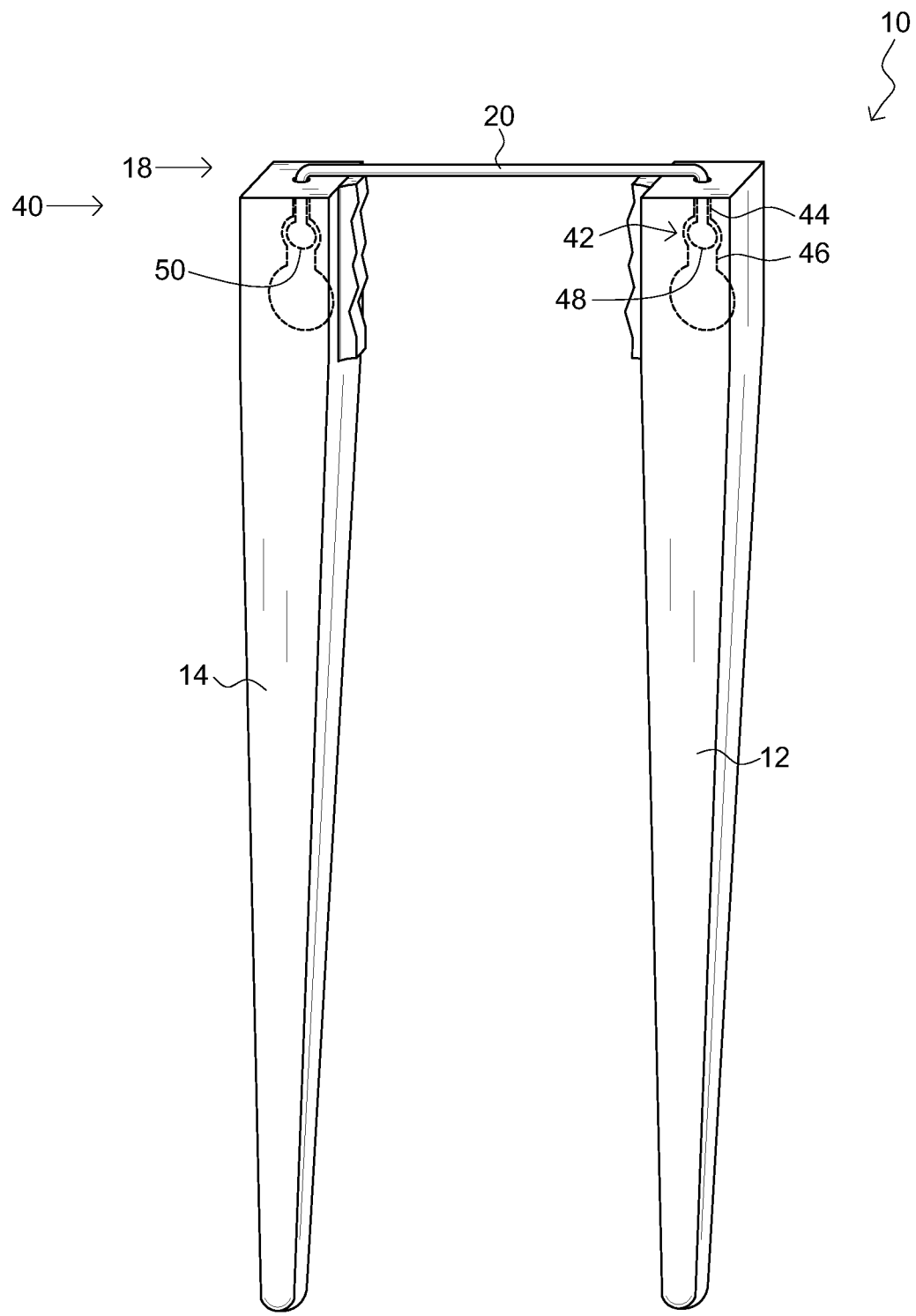
FIG. 2 is a perspective view of a flossing device in a second mode, according to one embodiment of the invention.

FIG. 2 is a flossing device in a second mode, according to one embodiment of the invention. There is shown a first elongated member 12 and a second elongated member 14 of a flossing device 10 in a second mode 40, wherein the elongated members are not connected by a connector and still connected by an extended floss string such that the floss string may be disposed between adjacent teeth of a user by manipulating the elongated members. The illustrated second mode is the mode wherein the connector is disconnected and the floss is able to be pulled tight into a position wherein the device may be used to clean between teeth.

The illustrated flossing device 10 includes a first elongated member 12 and a second elongated member 14 in a second mode 40. The illustrated second mode 40 includes the first elongated member 12 and the second elongated member 14 being uncoupled along a top end 18 of the members 12, 14. The first elongated member 12 and the second elongated member 14 each include a channel 42 disposed about the top end 18 of the first elongated member 12 and the second elongated member 14. The channel 42 includes a first cross-sectional spacing 46 and a second cross-sectional spacing 44. Cross-sectional spacing is that spacing that the end of the floss string experiences as it rest in the channel. A cross-sectional spacing substantially smaller than the end of the floss string will not permit the end of the floss string to pass therethrough while still permitting the floss string to move therethrough. A cross-sectional spacing that is substantially similar to the end of the floss string will permit the floss string to pass thereby when force is applied. A cross-sectional spacing substantially larger than the end of the floss string will permit the end of the floss string to move freely about the associate region.

The illustrated second cross-sectional spacing 44 is less than the first cross-sectional spacing 46, and the second cross-sectional spacing 44 is disposed closer to the top end 18, of the first elongated member 12 and the second elongated member 14, than the first cross-sectional spacing 46. The illustrated second cross-sectional spacing 44 is smaller than what will allow the end of the string to be pulled completely out of the channel, the string may be extended an amount when the sticks are pulled apart while still permitting the floss string to be taut while in use. The illustrated channel includes a pair of bulbous chambers wherein the end of the floss string may rest.

The flossing device 10 includes a floss string 20. The floss string 20 includes a first end 48 having an enlarged portion that is disposed within the channel 42 of the first elongated member 12. The first end 48 is sized to be substantially larger than the second cross-sectional spacing 44. The floss string 20 includes a second end 50 having an enlarged portion that is disposed within the channel 42 of the second elongated member 14. The second end 50 is sized to be substantially larger than the second cross-sectional spacing 44 of the second elongated member 14. The illustrated floss string 20 is knotted at both ends 48, 50, thus enlarging the end of the string as described above.

In operation of one embodiment of the invention, a user grasps a pair of elongated members of a flossing device at a tapered end. The user pulls the elongated members apart, thereby separating the elongated members at a top end and tightening a floss string between the elongated members. The user inserts the floss string in between teeth. The user manipulates each elongated member to position the floss string in between teeth to floss there between.

Figure 3:
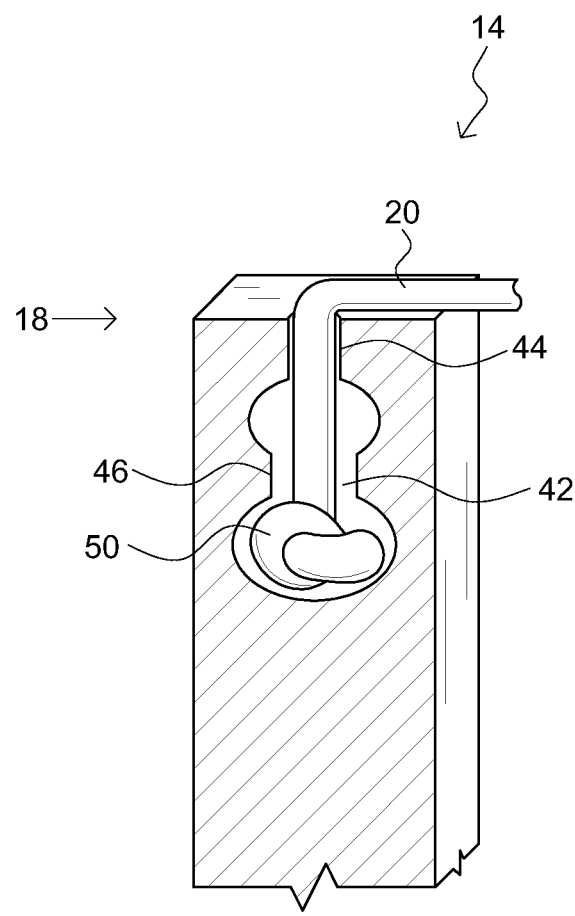
FIG. 3 is a partial cross-sectional view of a first elongated member of a flossing device, according to one embodiment of the invention.

FIG. 3 is a partial cross-sectional view of a first elongated member of a flossing device, according to one embodiment of the invention. There is shown a second elongated member 14 of a flossing device.

The flossing device includes a second elongated member 14. The illustrated second elongated member 14 includes a channel 42 that is disposed at a top end 18 of the second elongated member 14. The channel 42 includes a first cross-sectional spacing 46 and a second cross-sectional spacing 44. The second cross-sectional spacing 44 is less than the first cross-sectional spacing 46, and the second cross-sectional spacing 44 is closer to the top edge 18 of the second elongated member 14, than the first cross-sectional spacing 46. Accordingly, the end of the illustrated floss string may be pulled through and past the first cross-sectional spacing but not through or past the second cross-sectional spacing, thereby trapping the end of the floss string between regions 46 and 44 once pulled through spacing 46.

The flossing device includes a floss string 20. The illustrated floss string 20 includes a second end 50 having an enlarged portion that is disposed within the channel 42 of the second elongated member 14. The second end 50 is sized to be substantially larger than the second cross-sectional spacing 44 of the second elongated member 14. The illustrated second end 50 of the floss string 20 is knotted. The second end 50 rests in a chamber below the first cross-sectional spacing 46 in a first mode. The second end 50 in a second mode is retracted through the channel 42 formed by the first cross-sectional spacing 46 and secures or wedges into the chamber directly below second cross-sectional spacing 44, thereby permitting tightening of the floss string 20 between the pair of elongated members without releasing the floss string therefrom.

Figure 4:
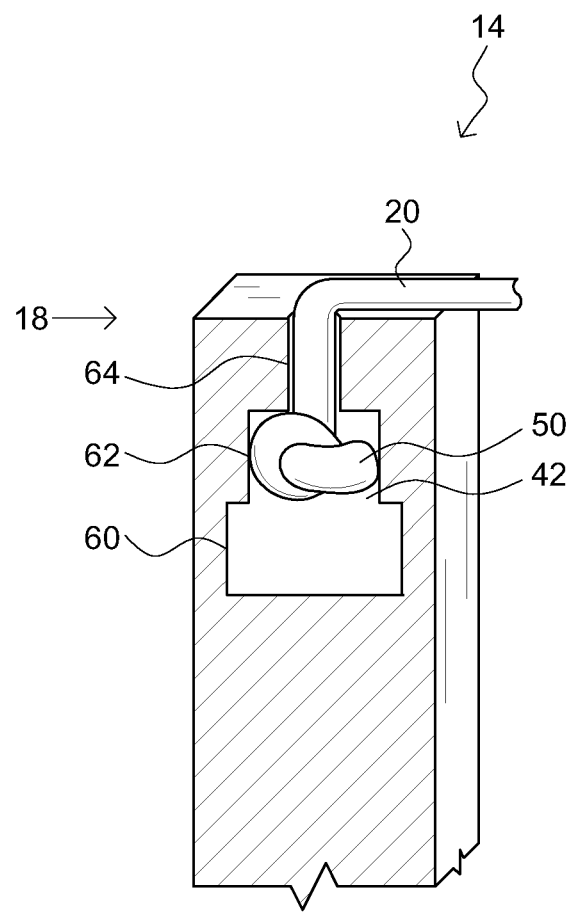
FIG. 4 is a partial cross-sectional view of a first elongated member of a flossing device, according to one embodiment of the invention.

FIG. 4 is a partial cross-sectional view of a first elongated member of a flossing device, according to one embodiment of the invention. There is shown a second elongated member 14 of a flossing device.

The flossing device includes a second elongated member. The illustrated second elongated member 14 includes a channel 42 that is disposed at a top end 18 of the second elongated member 14. The channel 42 includes a first cross-sectional spacing 60, a second cross-sectional spacing 62, and a third cross-sectional spacing 64. The third cross-sectional spacing 64 is less than the second cross-sectional spacing 62, and the second cross-sectional spacing is less than the first cross-sectional spacing 60. The third cross-sectional spacing 64 is closer to the top end 18 of the second elongated member 14 than the second cross-sectional spacing 62, and the second cross-sectional spacing 62 is closer to the top end 18 than the first cross-sectional spacing 60.

The flossing device includes a floss string 20. The illustrated floss string 20 includes a second end 50 having an enlarged portion that is disposed within the channel 42 of the second elongated member 14. The second end 50 is sized to be substantially larger than the third cross-sectional spacing 64. The second end 50 rests in the first cross-sectional spacing 60 in a first mode. The second end 50 in a second mode is retracted into the second cross-sectional spacing 62 and secures or wedges into the third cross-sectional spacing 64, thereby tightening the floss string 20 between the pair of elongated members.

The illustrated channel 42 of the flossing device includes a stepped chamber. The stepped chamber includes a base region 60, a middle region 62, and a top region 64. The base region 60 is substantially larger than the middle region 62, and the middle region 62 is larger than the top region 64. The top region 64 is disposed above the middle region 62 and the middle region 62 is disposed above the base region 60.

Figure 5:
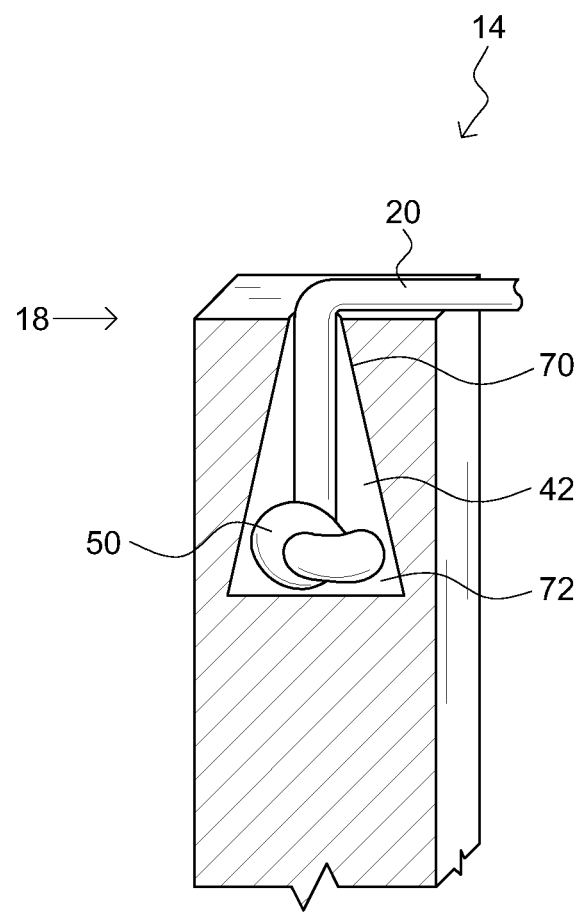
FIG. 5 is a partial cross-sectional view of a first elongated member of a flossing device, according to one embodiment of the invention.

FIG. 5 is a partial cross-sectional view of a first elongated member of a flossing device, according to one embodiment of the invention. There is shown a second elongated member 14 of a flossing device.

The flossing device includes a second elongated member 14. The second elongated member 14 includes a channel 42 disposed at a top end 18 of the second elongated member 14. The illustrated channel 42 includes a first cross-sectional spacing end 72 and a second cross-sectional spacing end 70. The second cross-sectional spacing end 70 is less than the first cross-sectional spacing end 72, and the second cross-sectional spacing end 70 is closer to the top end 18 of the second elongated member 14, than the first cross-sectional spacing end 72.

The flossing device includes a floss string 20. The floss string 20 includes second end 50 having an enlarged portion that is disposed within the channel 42 of the second elongated member 14. The second end 50 is sized to be substantially larger than the second cross-sectional spacing end 70. The second end 50 rests in the first cross-sectional spacing end 72 in a first mode. The second end 50 in a second mode is retracted into the channel 42 and secures or wedges into the second cross-sectional spacing 70, thereby tightening the floss string 20 between the pair of elongated members.

The illustrated channel 42 of the flossing device includes a frustoconical chamber. The frustoconical chamber includes a first end 70 and a second end 72, the second end 72 is includes a base that is configured to taper towards a peak of a first end 70.

Figure 6:
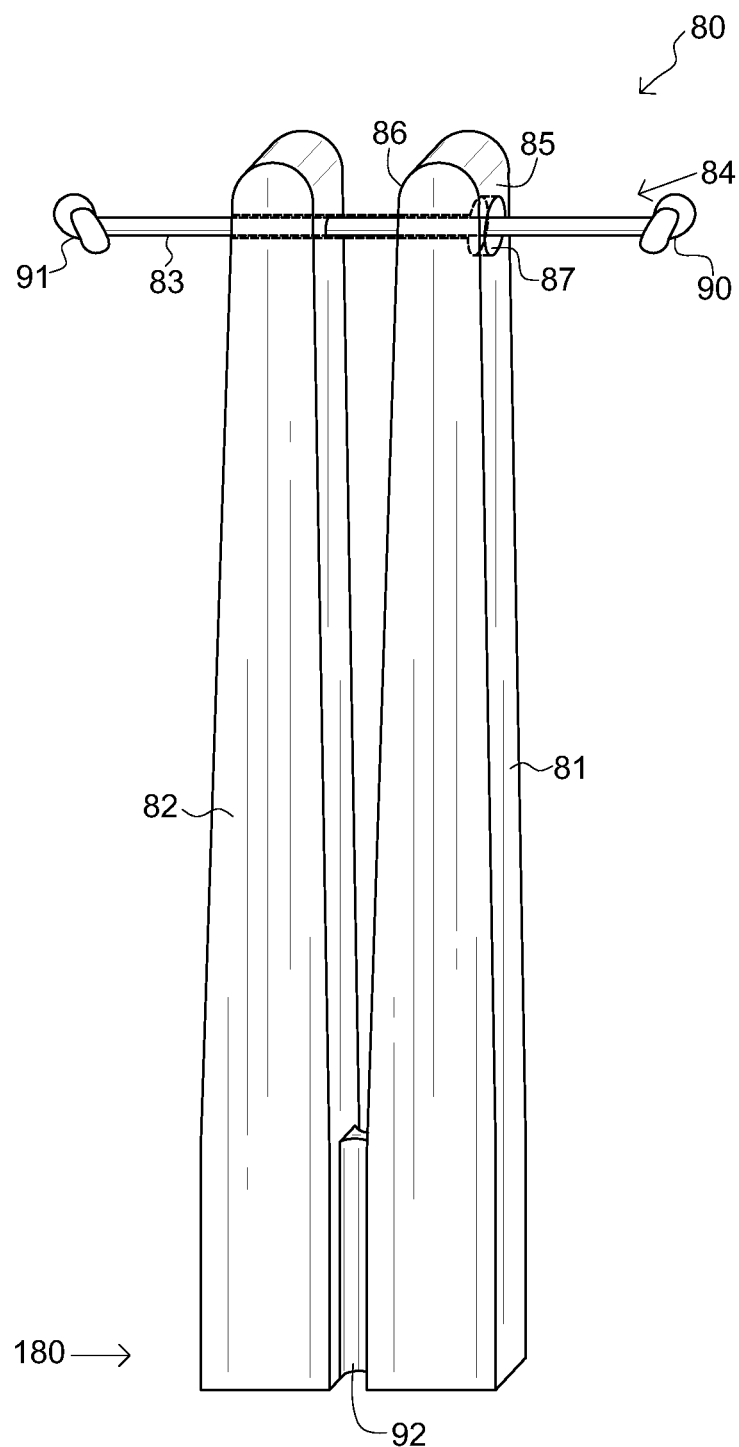
FIG. 6 is a perspective view of a flossing device in a first mode, according to one embodiment of the invention.

FIG. 6 is a perspective view of a flossing device in a first mode, according to one embodiment of the invention. There is shown a flossing device 80 having a first elongated member 81, a second elongated member 82, and a floss member 83.

The illustrated flossing device 80 consists of a first elongated member 81, wherein the first elongated member 81 includes a top region (or head region) 84 having an exterior side 85 and an interior side 86 opposite each other. The exterior side 85 is on an outside surface of the first elongated member 81. The first elongated member 81 includes an aperture 87 through the top region 84 between the exterior side 85 and the interior side 86. The aperture 87 is countersunk, thereby having a narrow channel coupled to an enlarged channel region. Being countersunk means that there is an aperture which includes an enlarged channel region adjacent to the exterior of the material through which the aperture exists, usually conical, which allows for an object to be place within the aperture to have an enlarged end portion rest within the countersink region. Countersinks are generally used with holes tapped for screws having enlarged heads, thus allowing the heads to be flush with the surrounding material. While various terms are used for such a structure and while such terms specify the shape of the enlarged aperture (e.g. counterbore means having an enlarged portion that is flat bottomed, i.e. cylindrical instead of conical). In this application, countersunk/countersink are intended to include all such variations of enlarged hole region shapes (conical, cylindrical, flat bottomed, hemispherical, etc.) and is not limited to just conical holes. The enlarged channel is on the exterior side of the first elongated member 81. While a countersink may be formed by milling/drilling, it may also be formed by other techniques, including but not limited to being part of an injection molding process, cutting, stamping, and the like and combinations thereof.

The illustrated flossing device 80 includes a second elongated member 82 removably coupled to the first elongated member 81 along the interior side 86 of a bottom region 180 of the first elongated member 81. The flossing device 80 includes a floss member 83 coupled to the second elongated member 82 and extending through the aperture 87 of the first elongated member 81. The floss member 83 includes a first enlarged stop member at an end distal from the second elongated member 82 and sized to fit within the enlarged channel (generally just barely and thereby getting stuck therein if wedged inside) but not fit through the narrow channel. Accordingly, when so fixed in place, the floss string is extended to its operational length and will not deviate from that position and will also not be pulled free from the elongated member(s) during use.

The illustrated second elongated member 82 includes a top region having an exterior side and an interior side opposite each other. The second elongated member 82 includes an aperture through the top region between the exterior side and the interior side. The aperture is countersunk, thereby having a narrow channel coupled to an enlarged channel. The enlarged channel 89 on the exterior side 85 of the first elongated member 81, and wherein the floss member 83 includes a second enlarged stop member 91 distal the first stop member 90 and sized to fit within the enlarged channel 89 of the second elongated member 82 but not fit through the narrow channel 88 of the second elongated member 82.

The illustrated first enlarged stop member 90 is sufficiently larger in an effective diameter (herein also described as being effective width, effective cross-sectional area, sized to be wedged, etc.) than the enlarged channel 89, in that the enlarged stop member must be bent, twisted, compacted, folded, or otherwise elastically deformed in order to fit therein, but not so large that such fitting is not practicable. Accordingly, the enlarged stop member may be wedged or otherwise stuck in place when pulled against the enlarged channel.

The illustrated first enlarged stop member 90 consists of an elastically deformable material (not necessarily completely elastic, but sufficiently elastic to be wedged when forced inside the enlarged channel), and is sized sufficiently large and sufficiently small to be wedged into the enlarged channel 89 when pulled thereagainst. The illustrated first enlarged stop member 90 consists of knotted floss. The bottom regions 180 of the illustrated first elongated member 81 and the illustrated second elongated member 82 are rectangular columns. The first elongated member 81 and the second elongated member 82 are removably coupled together by a breakaway bridge of material 92 therebetween disposed at a bottom region (herein also described as a foot or foot region) of the elongated members. The illustrated breakaway bridge of material is similar to those breakaway structures used in pairs of disposable chopsticks. The illustrated first elongated member 81 and the illustrated second elongated member 82 are formed from a single unitary piece of material, such as but not limited to being bamboo, plastic, or other similar materials.

Figure 7:
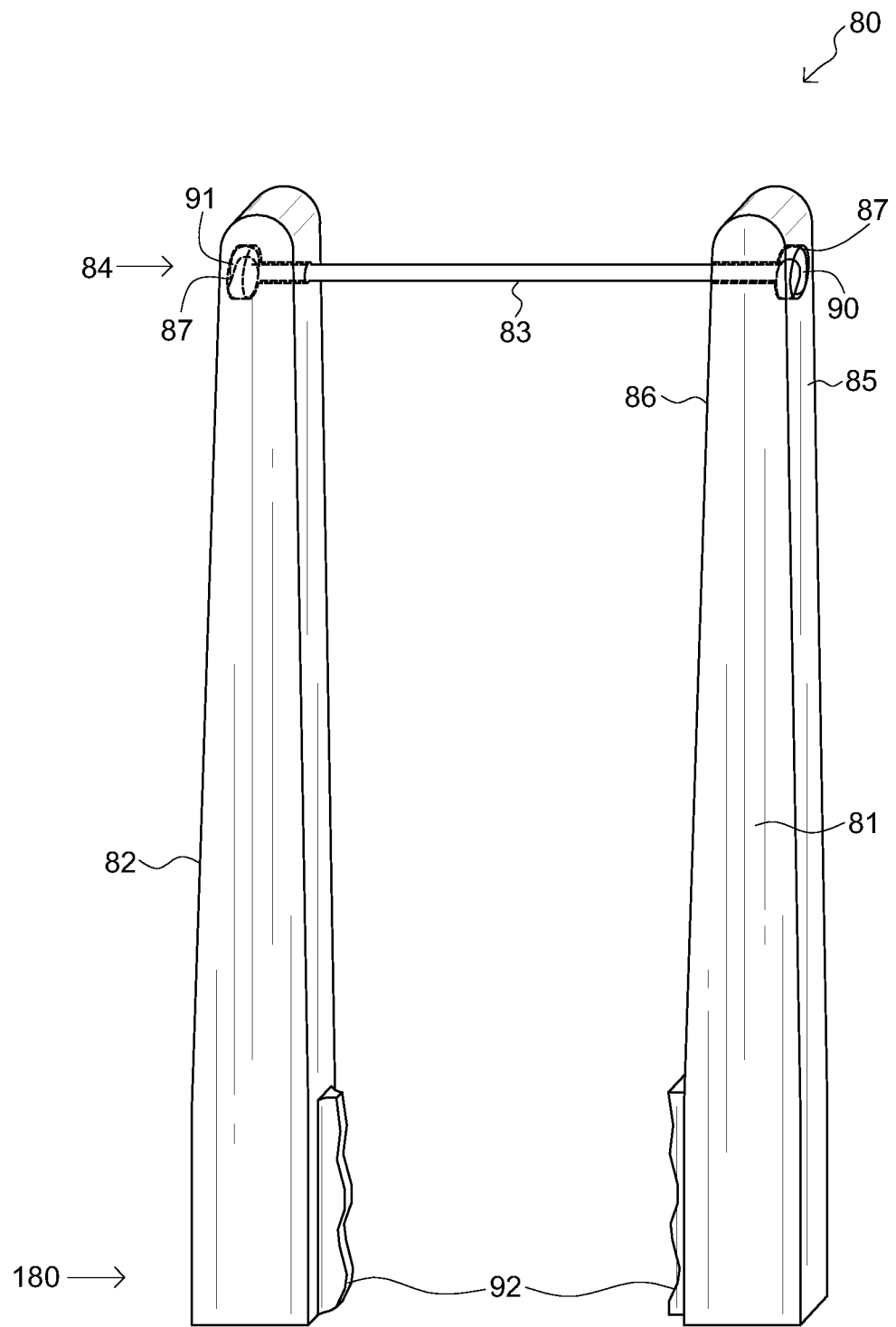
FIG. 7 is a perspective view of a flossing device in a second mode, according to one embodiment of the invention.

FIG. 7 is a perspective view of a flossing device in a second mode, according to one embodiment of the invention. There is shown a flossing device 80 having a pair of flossing sticks 81, 82. In the second mode, the elongated members are no longer coupled by the bridge (as it is broken or otherwise disconnected) and the floss string is wedged in place at its enlarged ends, which ends are wedged into countersunk holes at each elongated member head. The flossing device, in its second mode, is ready for use to clean between teeth.

The illustrated flossing device 80 includes a pair of flossing sticks 81, 82 coupled together by a bridge of breakaway material 92 at a bottom region 180 of the pair of flossing sticks 81, 82. In one non-limiting example, a bridge of breakaway material may include an elongated neck formed of a brittle material, such as but not limited to plastic and/or wood that may be narrower than the surrounding material, such that when pressure is applied to the region, a natural break occurs at the breakaway material instead of the surrounding structure. The pair of flossing sticks 81, 82 includes an aperture (hole) 87 through a top region 84 of a first floss stick 81 of the pair of floss sticks. The aperture 87 extends from an exterior surface 85 of the first floss stick 81 to a second floss stick 82 of the pair of floss sticks. The aperture 87 is countersunk at the exterior surface 85 and the exterior surface 85 being opposite the bridge of breakaway material 92. The pair of flossing sticks 81, 82 each includes a floss string 83 coupled to the second floss stick 82, disposed through the aperture 87 and extending out of the exterior surface 85 of the pair of floss sticks 81, 82. The floss string 83 includes a stop member sized to mate with the countersunk aperture when pulled thereagainst but to not pass through aperture, thereby coupling the pair of sticks 81, 82 together with floss 83 therebetween when the pair of flossing sticks 81, 82 are separated at the bridge of breakaway material 92. In one nonlimiting example, a stop member is an elastic material that is substantially larger than the floss and coupled thereto, such that the stop member cannot pass through the aperture. Such a stop member may be a knotted end of the floss and/or may include a rubber/plastic enlarged body that is coupled to the floss.

The illustrated second floss stick 82 includes a countersunk aperture 87 in communication with and opposite to the aperture 87 of the first floss stick 81. The illustrated pair of flossing sticks 81, 82 and bridge 92 are a singular formed material, such as but not limited to be carved out of a single piece of wood, fired as a single piece of porcelain, injection molded as a single piece of plastic, stamped as a single piece of metal and the like and combinations thereof. The stop member 90 is elastic and is sized to wedge within the countersunk aperture 87 such that, when tension is released from the pair of floss sticks 81, 82 when they are separated after having been pulled apart and the stop member 90 so wedged, the stop member 90 remains wedged within the countersunk aperture 87, thereby preventing the floss from retracting back through the aperture. The illustrated floss string 83 includes a second stop member 91 extending out of the countersunk aperture 87 of the second floss stick 82. However, it is contemplated that there may be a set of asymmetrically configured floss sticks wherein the floss is fixedly coupled to one of the floss sticks (glue, tied, integral, embedded, etc.) and wherein only one of the floss sticks includes an aperture and the floss only includes one stop member.

Figure 8:
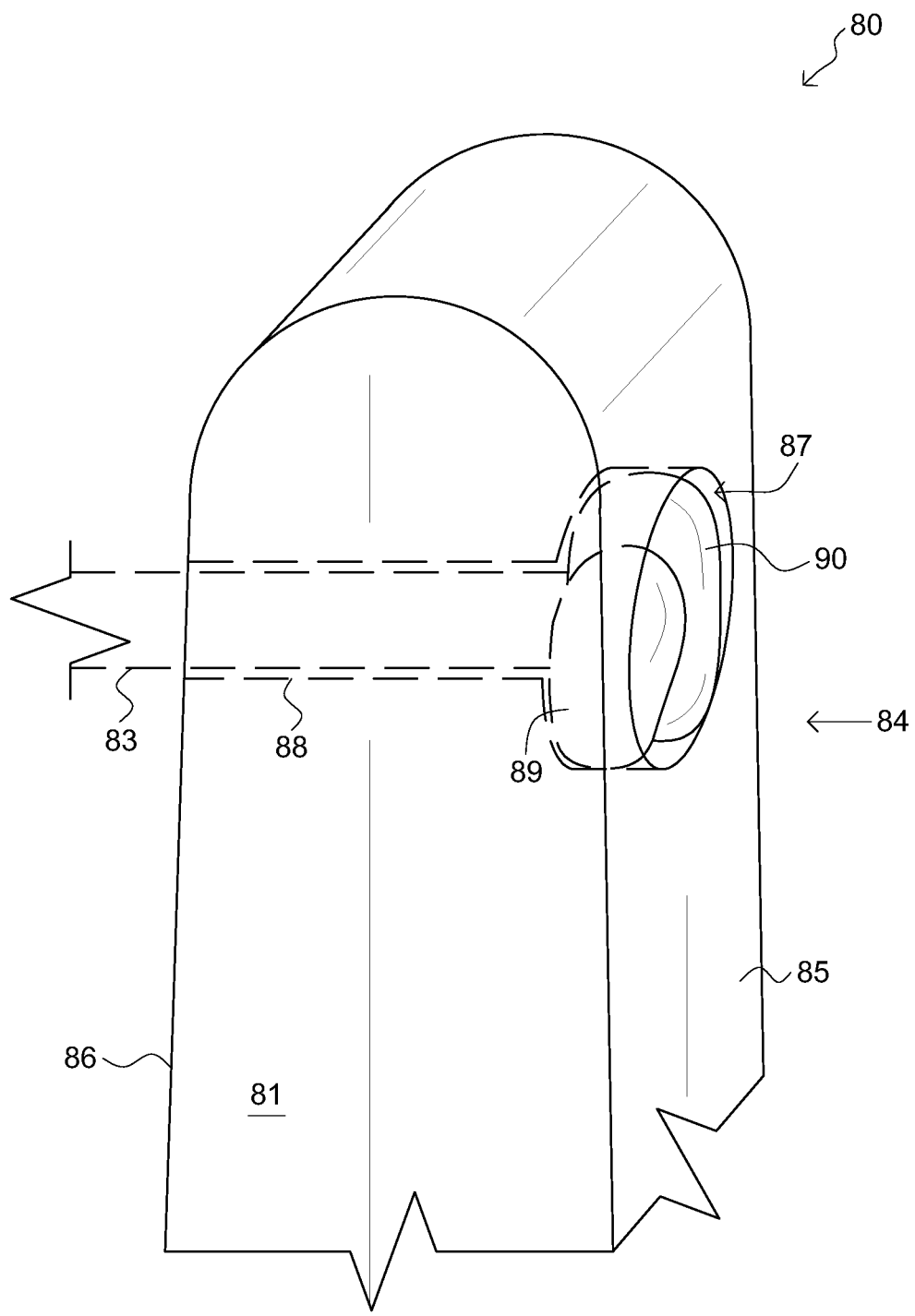
FIG. 8 is a partial cross-sectional view of a head region of a first elongated member of a flossing device, according to one embodiment of the invention.

FIG. 8 is a partial cross-sectional view of a head region of a first elongated member of a flossing device, according to one embodiment of the invention. There is shown a flossing device 80 having a first elongated member 81 and a floss member 83.

The illustrated flossing device 80 consists of a first elongated member 81, wherein the first elongated member 81 includes a top region 84 having an exterior side 85 and an interior side 86 opposite each other. The exterior side 85 is on an outside surface of the first elongated member 81. The first elongated member 81 includes an aperture 87 through the top region 84 between the exterior side 85 and the interior side 86. The aperture 87 is countersunk, thereby having a narrow channel 88 coupled to an enlarged channel 89. The enlarged channel 89 is on the exterior side of the first elongated member 81. The flossing device 80 includes a floss member 83 extending through the aperture 87 of the first elongated member 81.

The illustrated first enlarged stop member 90 is larger in cross-sectional area than the enlarged channel 89. The first enlarged stop member 90 consists of a deformable material, and is sized sufficiently small to be wedged into the enlarged channel 89 when pulled thereagainst. The first enlarged stop member 90 consists of knotted floss. The top region 84 of the first elongated member 81 is a rectangular column. The enlarged channel 89 transitions into the narrow channel 88 in a single stepped transition without a gradual decrease in channel width. The enlarged channel 89 transitions into the narrow channel 88 by a gradual decrease in channel width.

Figure 9:
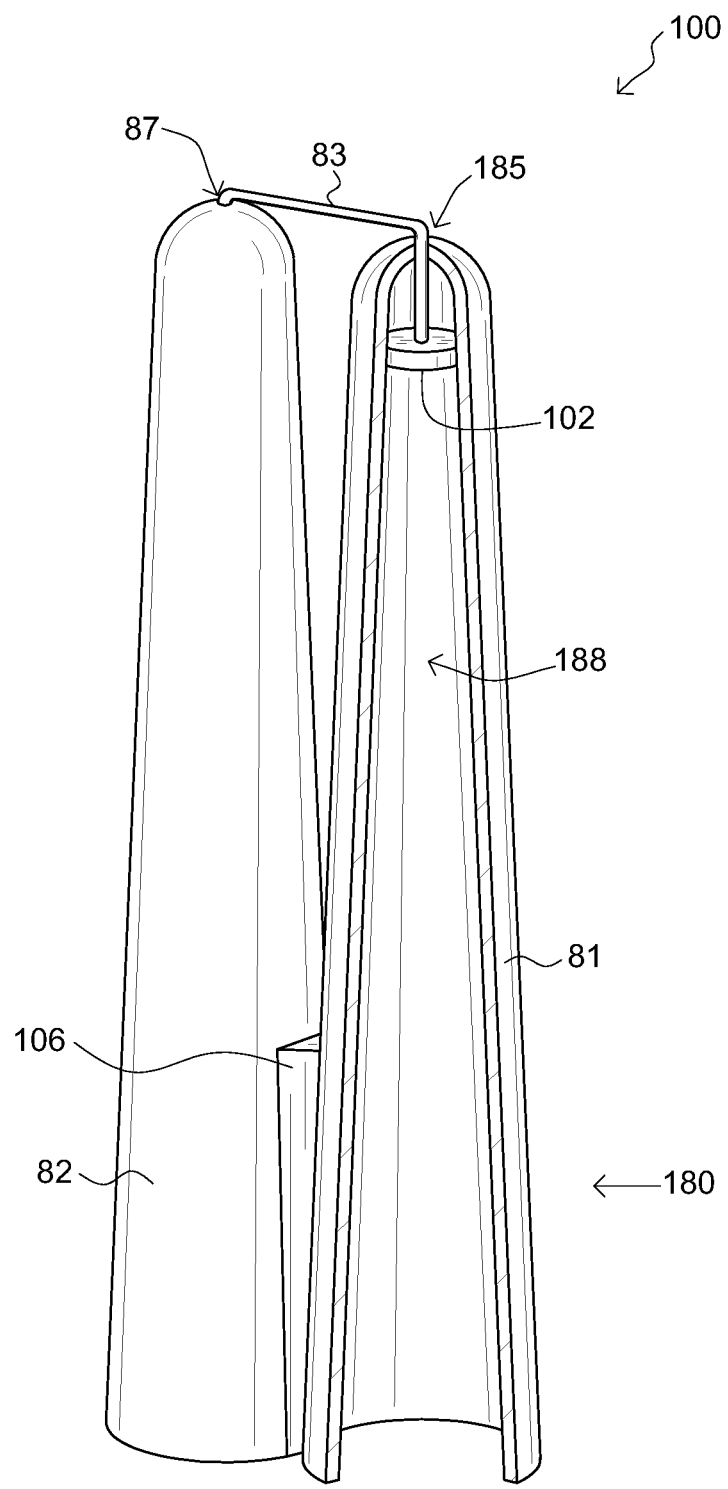
FIG. 9 is a perspective view of a flossing device showing a partial cross-sectional view of an elongated member in a first mode, according to one embodiment of the invention.

FIG. 9 is a perspective view of a flossing device showing a partial cross-sectional view of an elongated member in a first mode, according to one embodiment of the invention. There is shown a flossing device 100 including a first elongated member 81 and a second elongated member 82.

The illustrated flossing device 80 includes a first elongated member 81, wherein the first elongated member 81 includes a top region 84. The first elongated member 81 includes an aperture 87 through a top portion 185, wherein a floss member 83 extends upwardly therethrough. The first elongated member 81 includes a stop member 102 sized and shaped to be larger than the aperture 87, and configured to rest within the first elongated member 81. The aperture 87 is countersunk, thereby having a narrow channel coupled to an enlarged channel, wherein the narrow channel is the aperture and the enlarged channel is disposed within a cavity 188 of the first elongated member 81. In this illustrated example, the countersink extends through almost substantially all of the elongated member along its length, with only a very small narrow region at the tip of the elongated member, through which the floss extends but the stop member cannot pass through.

The illustrated flossing device 80 includes a second elongated member 82 removably coupled to the first elongated member 81 along a bottom region 180 of the first elongated member 81 and the second elongated member 82. The flossing device 80 includes a floss member 83 coupled to the second elongated member 82 and extending through the aperture 87 of the first elongated member 81. The floss member 83 includes a first enlarged stop member 102 at an end distal from the second elongated member 82 and sized to fit within the enlarged channel but not fit through the narrow channel, or aperture 87. The floss member 83 includes a second enlarged stop member, not shown, distal the first stop member 102 and sized to fit within an enlarged channel, or cavity, of the second elongated member 82 but not fit through the narrow channel, or aperture 87, of the second elongated member 82.

The illustrated first enlarged stop member 102 is larger in cross-sectional area than the enlarged channel or cavity 188. The first enlarged stop member 102 includes of a deformable material, and is sized sufficiently small to be wedged into the enlarged channel, or cavity 188 when pulled thereagainst. The first elongated member 81 and the second elongated member 82 are removably coupled together by a breakaway bridge of material 106 disposed therebetween about a bottom region 180. The first elongated member 81 and the second elongated member 82 are formed from a single unitary piece of material.

Figure 10:
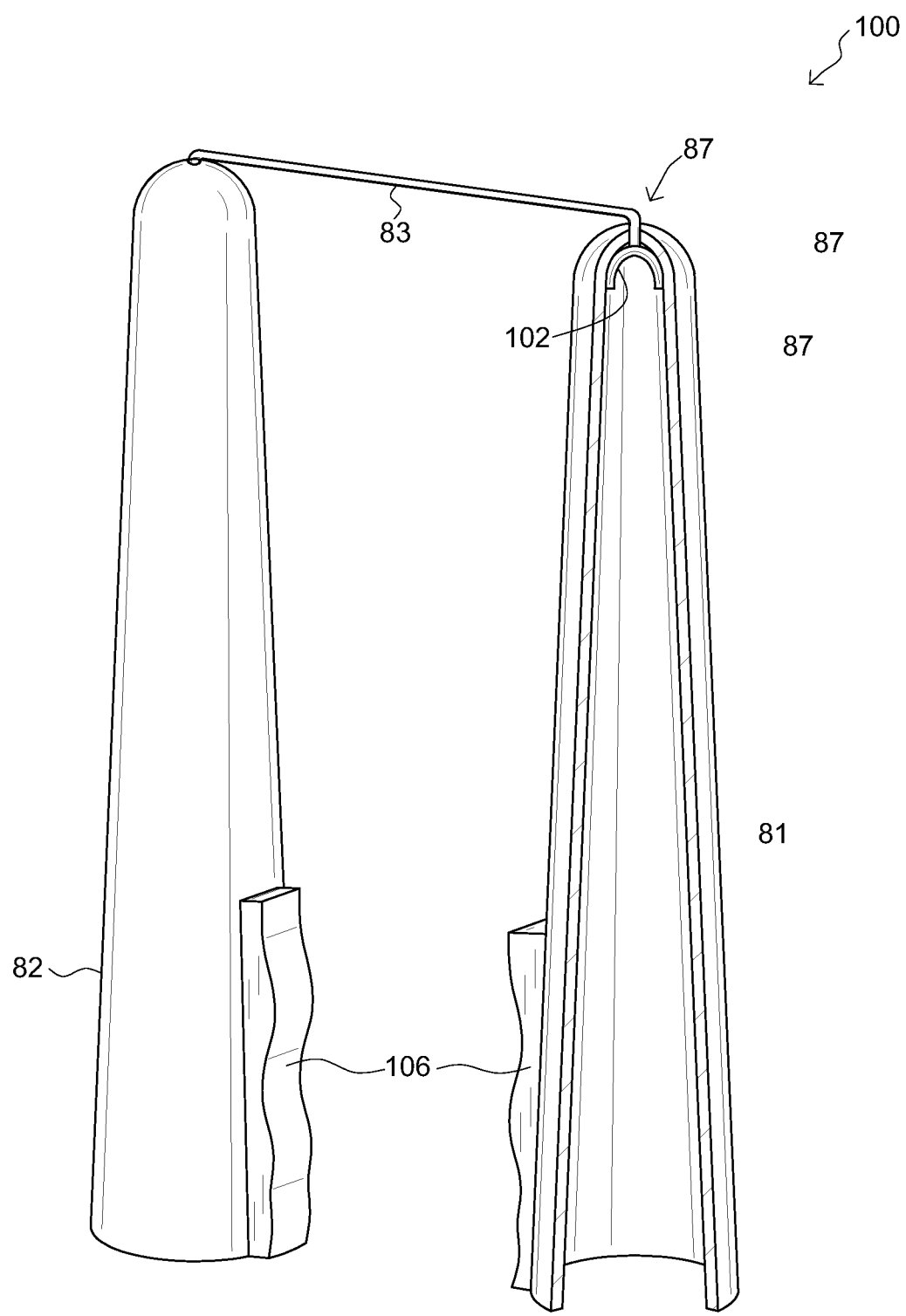
FIG. 10 is a perspective view of a flossing device showing a partial cross-sectional view of an elongated member in a second mode, according to one embodiment of the invention.

FIG. 10 is a perspective view of a flossing device showing a partial cross-sectional view of an elongated member in a second mode, according to one embodiment of the invention. There is shown a flossing device 100 including a first elongated member 81 and a second elongated member 82.

The illustrated flossing device 80 includes a first elongated member 81, wherein the first elongated member 81 includes a top region 84, wherein a floss member 83 is extending out from the first elongated member 81. The first elongated member 81 includes an aperture 87 through the top region 84, wherein the floss member 83 extends directly upwards therefrom. The aperture 87 is countersunk, thereby having a narrow channel coupled to an enlarged channel. In this illustrated example, the countersink extends through almost substantially all of the elongated member along its length, with only a very small narrow region at the tip of the elongated member, through which the floss extends but the stop member cannot pass through.

The illustrated flossing device 80 includes a second elongated member 82 removably coupled to the first elongated member 81 along a bottom region 180 of the first elongated member 81. The flossing device 80 includes a floss member 83 coupled to the second elongated member 82 and extending upwardly through the aperture 87 of the first elongated member 81. The floss member 83 includes a first enlarged stop member 102 at an end distal from the second elongated member 82 and sized to fit within the enlarged channel but not fit through the narrow channel or the aperture 87.

The second elongated member 82 includes an aperture through the top region and is also countersunk, thereby having a narrow channel coupled to an enlarged channel. The illustrated first enlarged stop member 102 is larger in cross-sectional area than the enlarged channel, or cavity 188. The first enlarged stop member 102 includes of a deformable material, and is sized sufficiently small to be wedged into the enlarged channel, or cavity 188 when pulled thereagainst, and not out through the aperture 87. The illustrated deformable material is a flexible disc that is oriented with its plane substantially perpendicular to the floss such that when pulled against the narrowing countersink the disc crumples and deformed to wedge itself thereinside. The first elongated member 81 and the second elongated member 82 are removably coupled together by a breakaway bridge of material 106 therebetween.

Figures 11, 12:
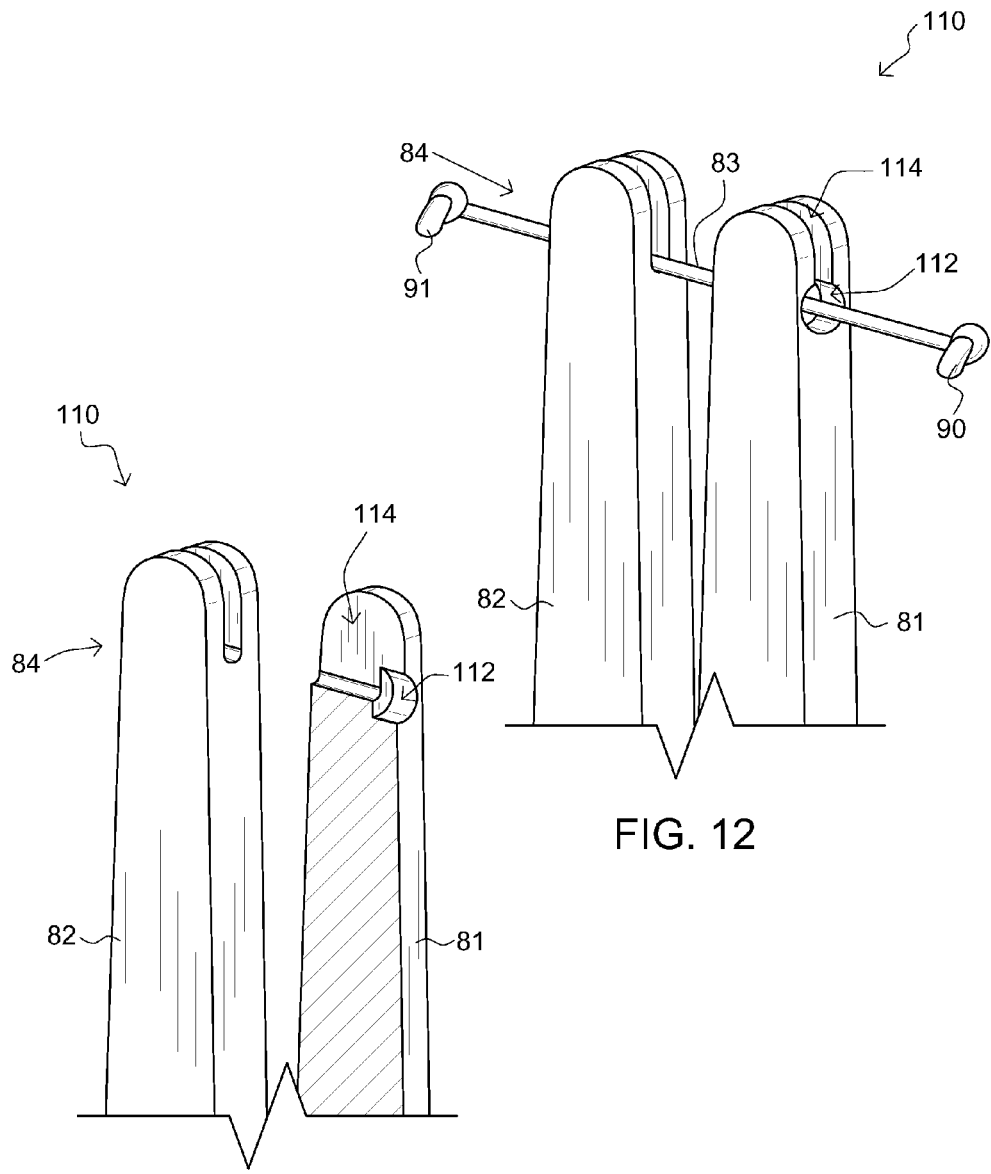
FIG. 11 is a partial perspective view of heads of a flossing device showing a partial cross-sectional view of a head of a flossing device, according to one embodiment of the invention.
FIG. 12 is a partial perspective view of heads of a flossing device, according to one embodiment of the invention.

FIG. 11 is a partial perspective view of heads of a flossing device showing a partial cross-sectional view of a head of a flossing device, according to one embodiment of the invention. There is shown a flossing device 110 including a first elongated member 81 and a second elongated member 82.

The illustrated flossing device 110 includes a first elongated member 81, wherein the first elongated member 81 includes a top region 84 having a channel 114 disposed therethrough. The channel 114 includes an open channel through a top portion of the first elongated member 81. The first elongated member 81 includes an aperture 112 in communication with the channel 114 and configured to receive a floss member 83 through the top region 84. The aperture 112 is countersunk, thereby having a narrow channel, such as the aperture 112 coupled to the channel 114.

The illustrated flossing device 80 includes a second elongated member 82 removably coupled to the first elongated member 81. The flossing device 80 includes a floss member 83 coupled to the second elongated member 82 and extending through the aperture 112 and channel 114 of the first elongated member 81. The floss member 83 includes a first enlarged stop member at an end distal from the second elongated member 82 and sized to fit within the channel 114 but not fit through the narrow channel of the aperture 112.

FIG. 12 is a partial perspective view of heads of a flossing device, according to one embodiment of the invention. There is shown a flossing device 110 including a first elongated member 81 and a second elongated member 82.

The illustrated flossing device 110 includes a first elongated member 81, wherein the first elongated member 81 includes a top region 84 having a channel 114 disposed therethrough. The first elongated member 81 includes an aperture 112 in communication with the channel 114 and configured to receive a floss member 83 through the top region 84. The aperture 112 is countersunk, thereby having a narrow channel, such as the aperture 112 coupled to the channel 114.

The illustrated flossing device 80 includes a second elongated member 82 removably coupled to the first elongated member 81. The flossing device 80 includes a floss member 83 coupled to the second elongated member 82 and extending through the aperture 112 and channel 114 of the first elongated member 81. The floss member 83 includes a first enlarged stop member at an end distal from the second elongated member 82 and sized to fit within the channel 114 but not fit through the narrow channel of the aperture 112.

The illustrated floss member 83 includes a first enlarged stop member 90 and a second enlarged stop member 91 distal the first stop member 90 and sized to fit within a channel of the second elongated member 82 but not fit through the narrow channel of the aperture of the second elongated member 82. The illustrated first enlarged stop member 90 is larger in cross-sectional area than the channel 114. The first enlarged stop member 90 consists of a deformable material, and is sized sufficiently small to be wedged into the channel 114 when pulled thereagainst. The first enlarged stop member 90 consists of knotted floss.

Advantageously, in the example illustrated in FIGS. 11 and 12, a length of floss string may be used and then removed from the elongated members through the channel 114. A second floss string may be applied to the elongated members through channel 114, thereby permitting reusability of elongated members while having disposable floss strings. While the illustrated example allows for floss strings to be trapped "inside" elongated members, those elongated members are topologically equivalent to spheres. In other examples provided in other figures herein, there is no additional channel 114 which permits removal of floss strings, the countersunk apertures are not in communication with any other channels, and their associated elongated members are each topologically equivalent to toroid.

Figures 13, 14:
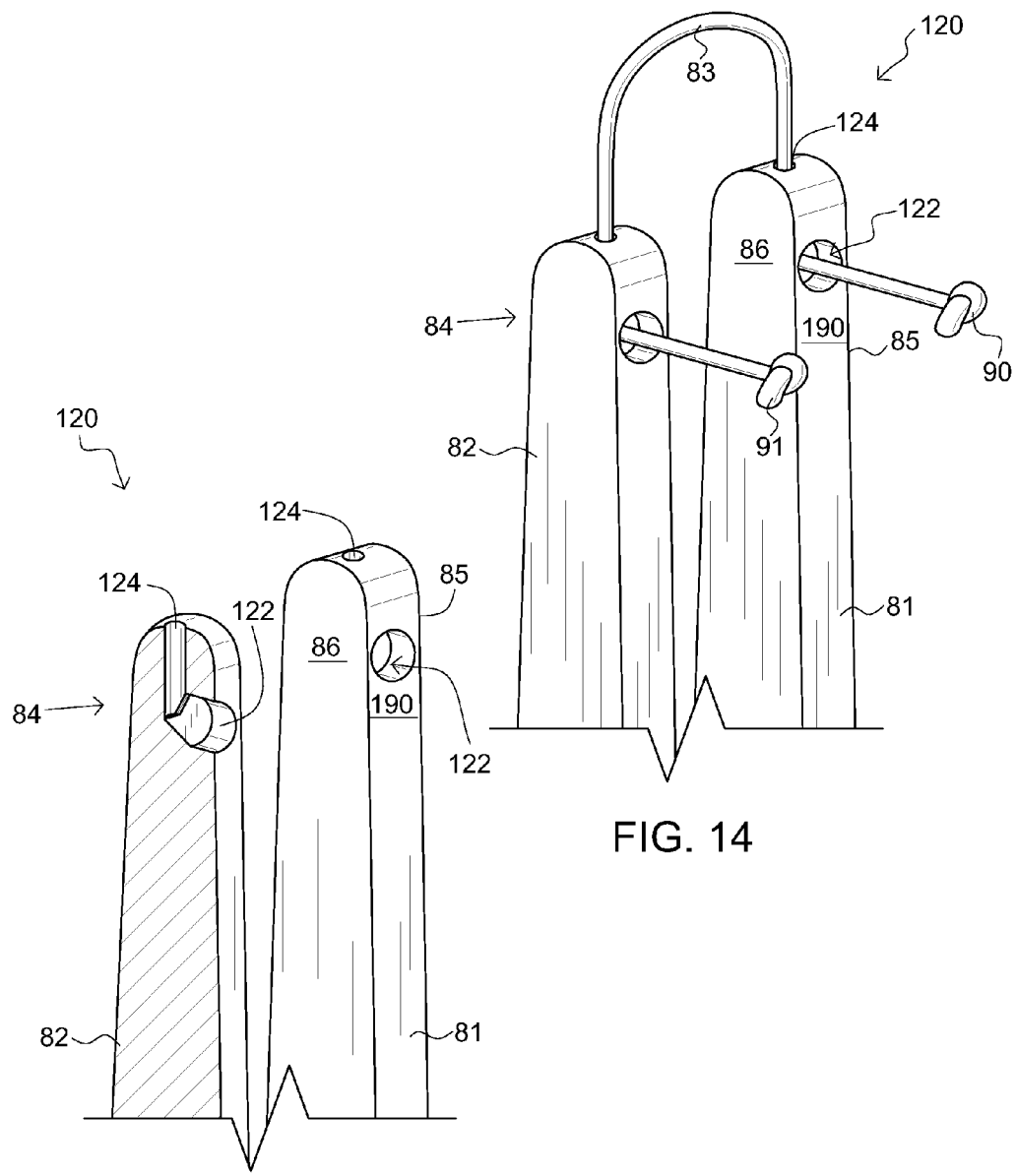
FIG. 13 is a partial perspective view of heads of a flossing device showing a partial cross-sectional view of a head of a flossing device, according to one embodiment of the invention.
FIG. 14 is a partial perspective view of heads of a flossing device, according to one embodiment of the invention.

FIG. 13 is a partial perspective view of heads of a flossing device showing a partial cross-sectional view of a head of a flossing device, according to one embodiment of the invention. There is shown a flossing device 120 including a first elongated member 81 and a second elongated member 82. In the illustrated example, the countersunk aperture includes a bend wherein the countersink is not oriented in the same direction as the narrow channel with which it is connected. There is approximately a 90 degree bend in the channel that occurs near the transition between the countersink and the narrow channel. This allows the floss to extend from the tip of the head of the elongated members, while the enlarged stop member is oriented out a side of the elongated member.

The illustrated flossing device 80 includes a first elongated member 81, wherein the first elongated member 81 includes a top region 84. The first elongated member 81 includes an aperture 122 through a side surface 190 between an exterior side 85 and an interior side 86. The aperture 87 is countersunk, thereby having a narrow channel of the aperture 122 coupled to an enlarged channel 124. The illustrated enlarged channel 124 is in communication with the aperture 122, wherein the enlarged channel 124 extends upwardly from the aperture 122 and out through a top region of the first elongated member 81.

The illustrated flossing device 80 includes a second elongated member 82 removably coupled to the first elongated member 81. The flossing device 80 includes a floss member 83 coupled to the second elongated member 82 and extending through the enlarged channel 124 of the first elongated member 81. The illustrated second elongated member 82 includes a top region 84 having an exterior side 85 and an interior side 86 opposite each other. The second elongated member 82 includes an aperture 122 through the top region 84 between the exterior side 85 and the interior side 86. The aperture 122 is countersunk, thereby having a narrow channel coupled to an enlarged channel 124.

FIG. 14 is a partial perspective view of heads of a flossing device, according to one embodiment of the invention. There is shown a flossing device 120 including a first elongated member 81 and a second elongated member 82. In the illustrated example, the countersunk aperture includes a bend wherein the countersink is not oriented in the same direction as the narrow channel with which it is connected. There is approximately a 90 degree bend in the channel that occurs near the transition between the countersink and the narrow channel. This allows the floss to extend from the tip of the head of the elongated members, while the enlarged stop member is oriented out a side of the elongated member.

The illustrated flossing device 80 includes a first elongated member 81, wherein the first elongated member 81 includes a top region 84. The first elongated member 81 includes an aperture 122 through a side surface 190 between an exterior side 85 and an interior side 86. The aperture 87 is countersunk, thereby having a narrow channel of the aperture 122 coupled to an enlarged channel 124. The illustrated enlarged channel 124 is in communication with the aperture 122, wherein the enlarged channel 124 extends upwardly from the aperture 122 and out through a top region of the first elongated member 81.

The illustrated flossing device 80 includes a second elongated member 82 removably coupled to the first elongated member 81. The flossing device 80 includes a floss member 83 coupled to the second elongated member 82 and extending through the enlarged channel 124 of the first elongated member 81. The floss member 83 includes a first enlarged stop member 90 at an end distal from the second elongated member 82 and sized to fit within the enlarged channel 124 but not fit through the narrow channel 112.

The illustrated second elongated member 82 includes a top region 84 having an exterior side 85 and an interior side 86 opposite each other. The second elongated member 82 includes an aperture 122 through the top region 84 between the exterior side 85 and the interior side 86. The aperture 122 is countersunk, thereby having a narrow channel coupled to an enlarged channel 124. The floss member 83 includes a second enlarged stop member 91 distal the first stop member 90 and sized to fit within the enlarged channel of the second elongated member 82 but not fit through the narrow channel of the second elongated member 82.

The illustrated first enlarged stop member 90 is larger in effective width than the enlarged channel 89. The first enlarged stop member 90 consists of a deformable material, and is sized sufficiently small to be wedged into the enlarged channel 89 when pulled thereagainst. The first enlarged stop member 90 consists of knotted floss.

Figures 15, 16:
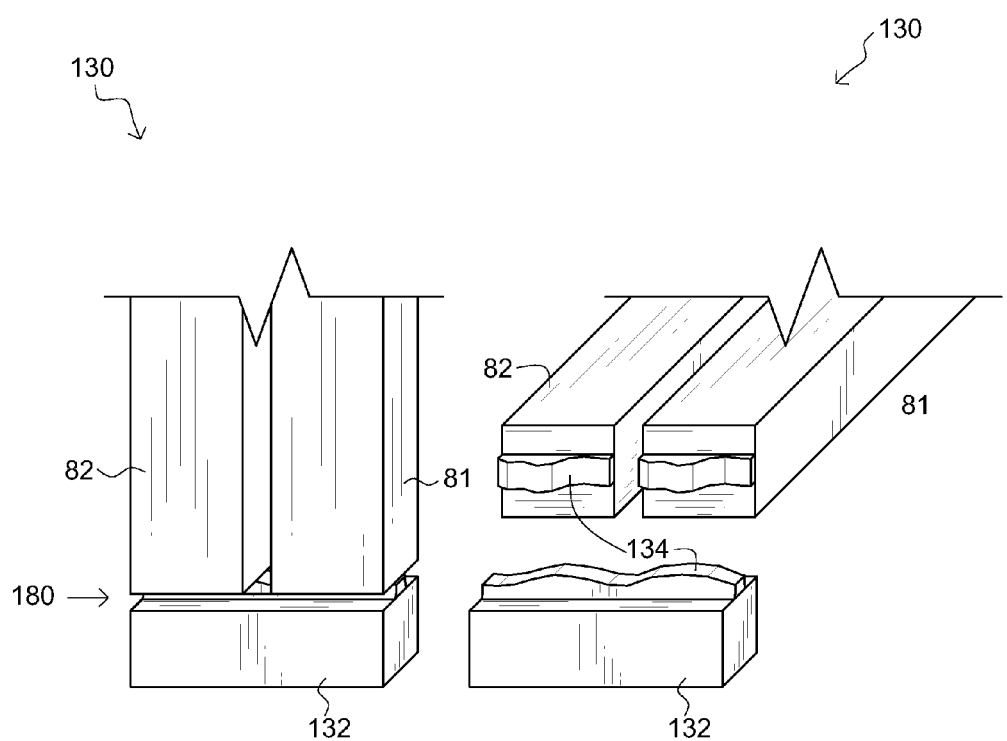
FIG. 15 is a partial perspective view of feet of a flossing device in a first mode, according to one embodiment of the invention.
FIG. 16 is a partial perspective view of feet of a flossing device in a second mode, according to one embodiment of the invention.

FIGS. 15 and 16 are partial perspective views of feet of a flossing device in a first mode and second mode respectively, according to one embodiment of the invention. There is shown a flossing device 130 including a first elongated member 81 and a second elongated member coupled by a breakaway bridge 134.

The illustrated flossing device 130 includes a first elongated member 81, wherein the first elongated member 81 includes a bottom region 180. The flossing device 130 includes a second elongated member 82 removably coupled to the first elongated member 81 by a coupling member 132. The bottom regions 180 of the first elongated member 81 and the second elongated member 82 are rectangular columns. The first elongated member 81 and the second elongated member 82 are removably coupled together by a breakaway bridge of material 134 configured to break the first elongated member 81 from the second elongated member 82 and from the coupling member 132. The first elongated member 81 and the second elongated member 82 are formed from a single unitary piece of material.

Figure 17:
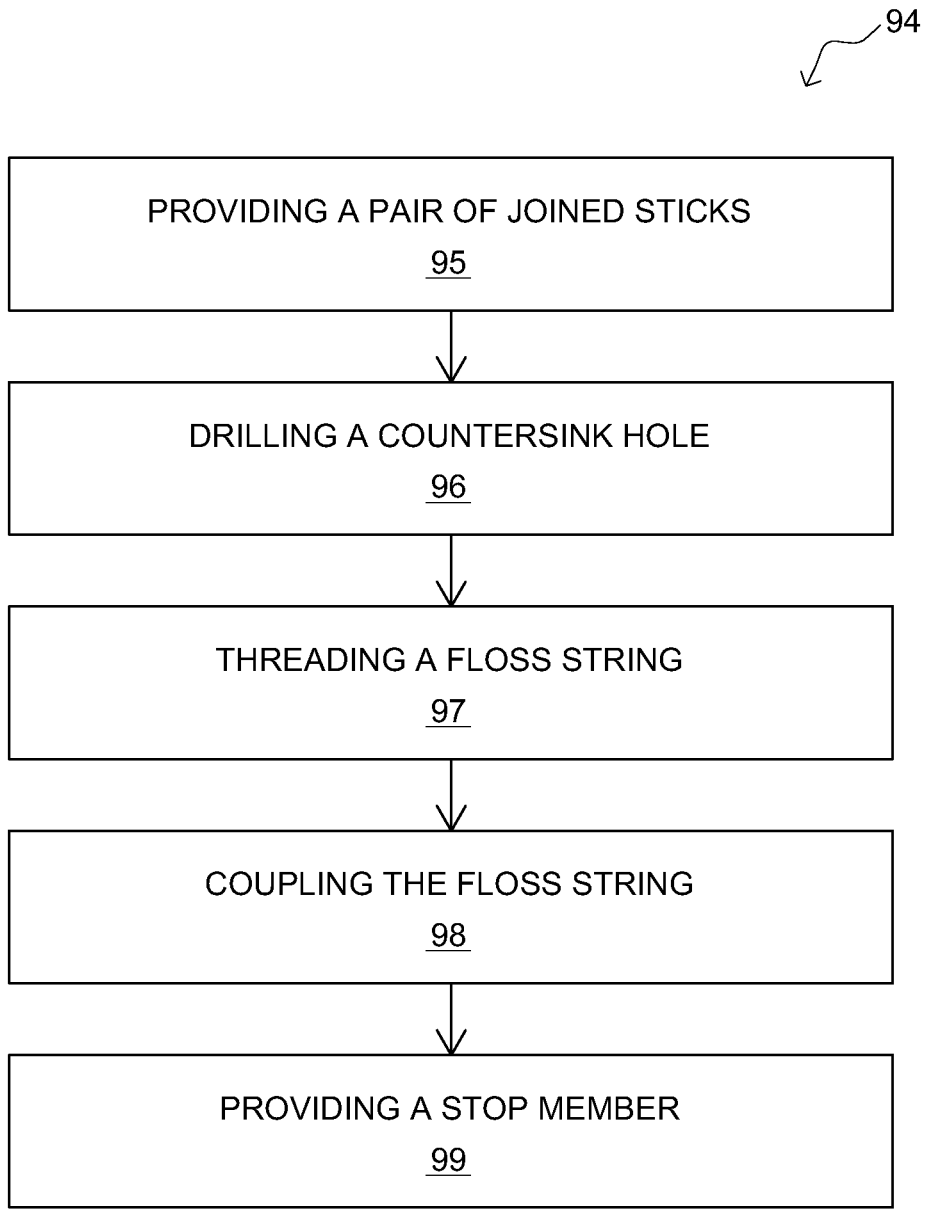
FIG. 17 is a flow diagram of a method of manufacturing a flossing device, according to one embodiment of the invention.

FIG. 17 is a flow diagram of a method of manufacturing a flossing device, according to one embodiment of the invention. There is shown a method of manufacturing a flossing device 94.

The illustrated method of manufacturing a flossing device 94 includes the step of providing a pair of joined sticks 95, including a first stick and a second stick. Such may include providing and/or manufacturing one or more sticks or sets of sticks as described herein. The sticks are joined side by side at their heads by a breakable bridge therebetween. The method 94 includes the step of drilling a countersunk hole through both of the heads of the joined sticks 96, wherein the countersunk region is at an exterior surface of the first stick. Such drilling is generally accomplished by using a countersinking drill bit and/or by using a plurality of differently shaped drill bits. Such a countersunk structure may be stepped as in the illustrated examples and/or it may be diagonal/slanted/gradual wherein a conical shaped drill bit is used. The method 94 includes threading a floss string through the countersunk hole 97. The method 94 includes the step of coupling the floss string to the second stick 98, such as but not limited to by glue, staple, rivet, and/or threading floss through an aperture through the second stick and tying, knotting, attaching a stop member or otherwise fixing the floss to the second stick. The method 94 further includes the step of providing a stop member at an end of the floss string 99. The stop member is configured to mate with the countersunk hole when pulled thereagainst but not to pass therethrough. Accordingly, the stop member may be sized to be slightly larger than the countersunk hole so that it may be wedged therein and fit tightly therein.

The method of manufacturing a flossing device includes the step of drilling a second countersunk region in the second stick opposite the first stick. The step of coupling the floss string to the second stick 98 includes providing a second stop member at an opposite end of the floss string. The stop member consists essentially of knotting the floss string. The illustrated joined sticks herein are shaped like chopsticks. The step of providing a pair of joined sticks 95 includes forming the pair of joined sticks from a single material, such as but not limited to plastic, wood, metal, ceramic, clay, composite, and the like and combinations thereof.

The present application presents a method of flossing using a flossing device, comprising one or more of the steps of: grasping a pair of elongated members coupled together along an end; pulling the elongated members apart until the coupling therebetween breaks; pulling the elongated members apart until a floss string therebetween retracts to a usable length; and/or inserting the floss string in between teeth. Such a method may also include pulling the pair of elongated members until a knot of the floss string is wedged within a channel of an elongated member; pulling the pair of elongated members until a pair of knots of the floss string is wedged within a channel of the pair of elongated members; removing and replacing a seal of the pair of elongated members; and/or manipulating the pair of elongated members in between teeth, from a side base of a tooth to the top side of a tooth and therebetween.

Floss string may be retracted using one or more of the following structures/systems: spools, springs or other bias members, fixed attachment with extra floss length stored in a chamber (such as by coiling), floss string having a portion thereof being sufficiently elastic and/or of sufficient length to provide usable retraction.

Figure 18:
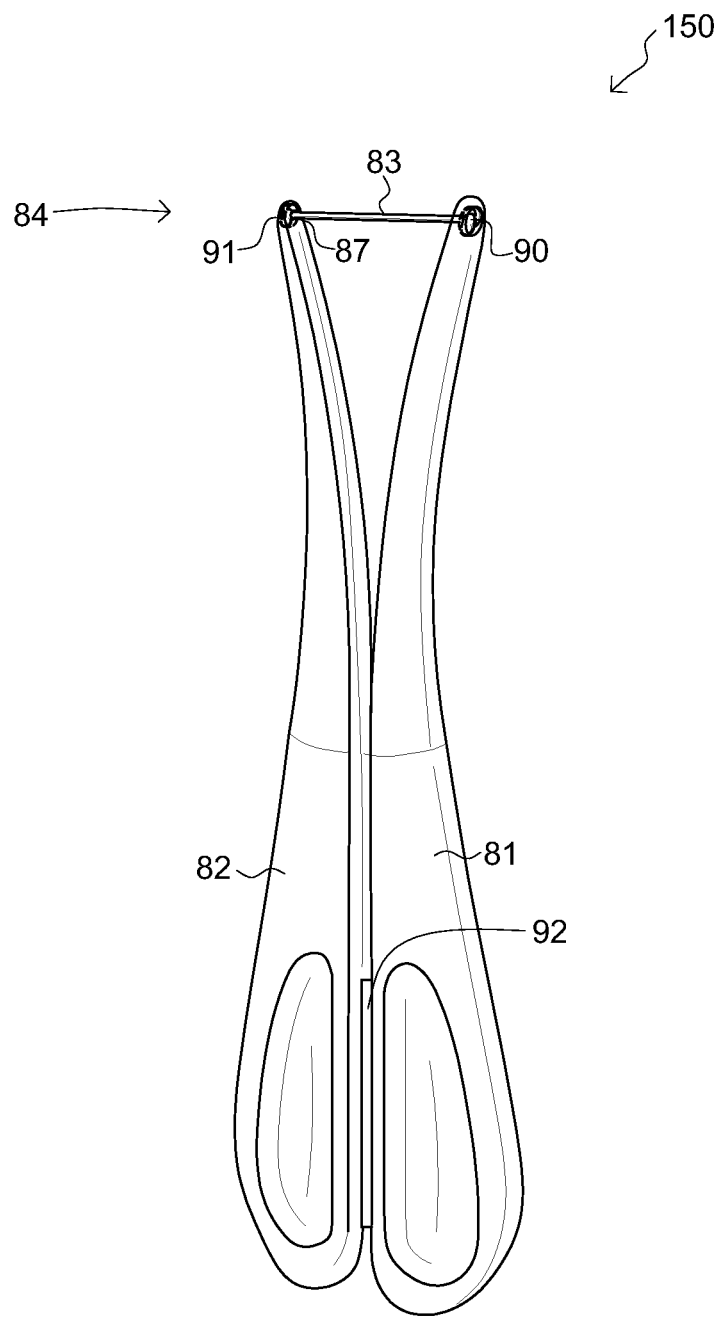
FIG. 18 is a perspective view of a flossing device, according to one embodiment of the invention.

FIG. 18 is a perspective view of a flossing device, according to one embodiment of the invention. There is shown a flossing device 150 including a first elongated member 81 and a second elongated member 82.

The illustrated flossing device 130 includes a first elongated member 81, wherein the first elongated member 81 includes a top region 84. The first elongated member 81 includes an aperture 87 through the top region 84. The aperture 87 is configured to enable a floss member 83 to pass therethrough but not completely.

The illustrated flossing device 130 includes a second elongated member 82 removably coupled to the first elongated member 81. The flossing device 130 includes a floss member 83 coupled to the second elongated member 82 and extending through the aperture 87 of the first elongated member 81. The floss member 83 includes a first enlarged stop member 90 at an end distal from the second elongated member 82 and sized to fit within the aperture 87 but not completely therethrough.

The illustrated second elongated member 82 includes a top. The second elongated member 82 includes an aperture 87 through the top region 84, wherein the floss member 83 includes a second enlarged stop member 91 distal the first stop member 90 and sized to fit within the aperture 87 but not completely therethrough.

The illustrated first enlarged stop member 90 is larger in cross-sectional area than the aperture 87. The first enlarged stop member 90 consists of a deformable material, and is sized sufficiently small to be wedged into the enlarged channel 89 when pulled thereagainst. The first enlarged stop member 90 consists of knotted floss. The first elongated member 81 and the second elongated member 82 are removably coupled together by a breakaway bridge of material 92 therebetween. The first elongated member 81 and the second elongated member 82 are formed from a single unitary piece of material.

Figure 19:
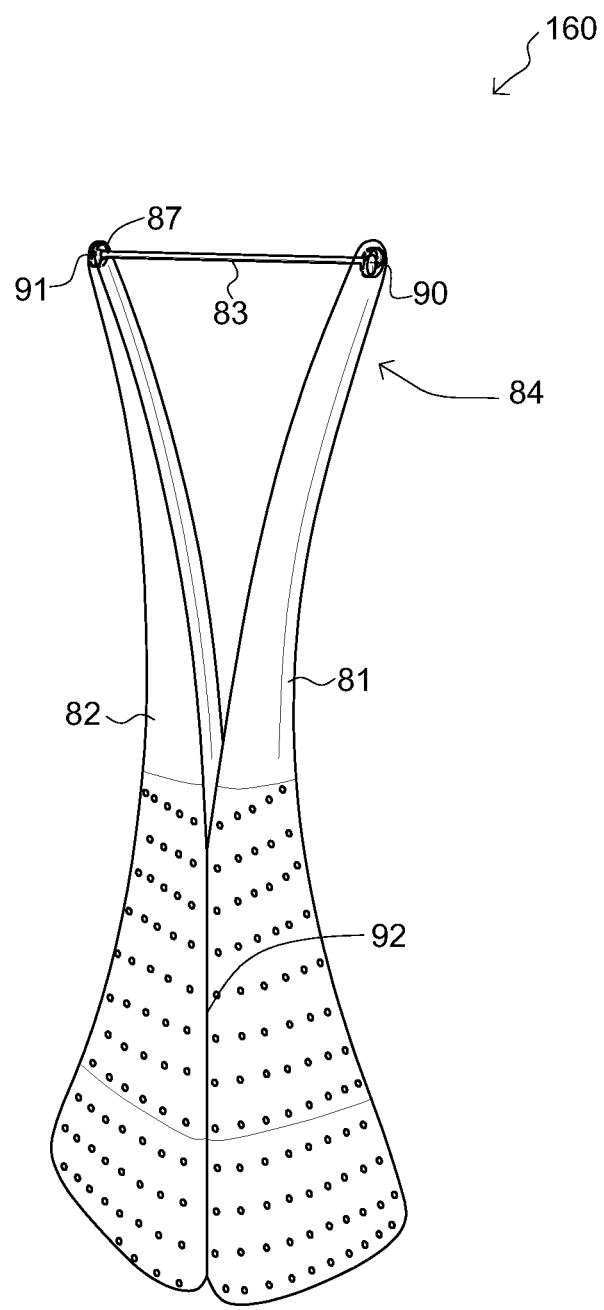
FIG. 19 is a perspective view of a flossing device, according to one embodiment of the invention.

FIG. 19 is a perspective view of a flossing device, according to one embodiment of the invention. There is shown a flossing device 160 including a first elongated member 81 and a second elongated member 82.

The illustrated flossing device 160 includes a first elongated member 81, wherein the first elongated member 81 includes a top region 84. The first elongated member 81 includes an aperture 87 through the top region 84. The aperture 87 is configured to enable a floss member 83 to pass therethrough but not completely.

The illustrated flossing device 160 includes a second elongated member 82 removably coupled to the first elongated member 81. The flossing device 160 includes a floss member 83 coupled to the second elongated member 82 and extending through the aperture 87 of the first elongated member 81. The floss member 83 includes a first enlarged stop member 90 at an end distal from the second elongated member 82 and sized to fit within the aperture 87 but not completely therethrough.

The illustrated second elongated member 82 includes a top. The second elongated member 82 includes an aperture 87 through the top region 84, wherein the floss member 83 includes a second enlarged stop member 91 distal the first stop member 90 and sized to fit within the aperture 87 but not completely therethrough.

The illustrated first enlarged stop member 90 is larger in cross-sectional area than the aperture 87. The first enlarged stop member 90 consists of a deformable material, and is sized sufficiently small to be wedged into the enlarged channel 89 when pulled thereagainst. The first enlarged stop member 90 consists of knotted floss. The first elongated member 81 and the second elongated member 82 are removably coupled together by a breakaway bridge of material 92 therebetween. The first elongated member 81 and the second elongated member 82 are formed from a single unitary piece of material.

Figure 20:
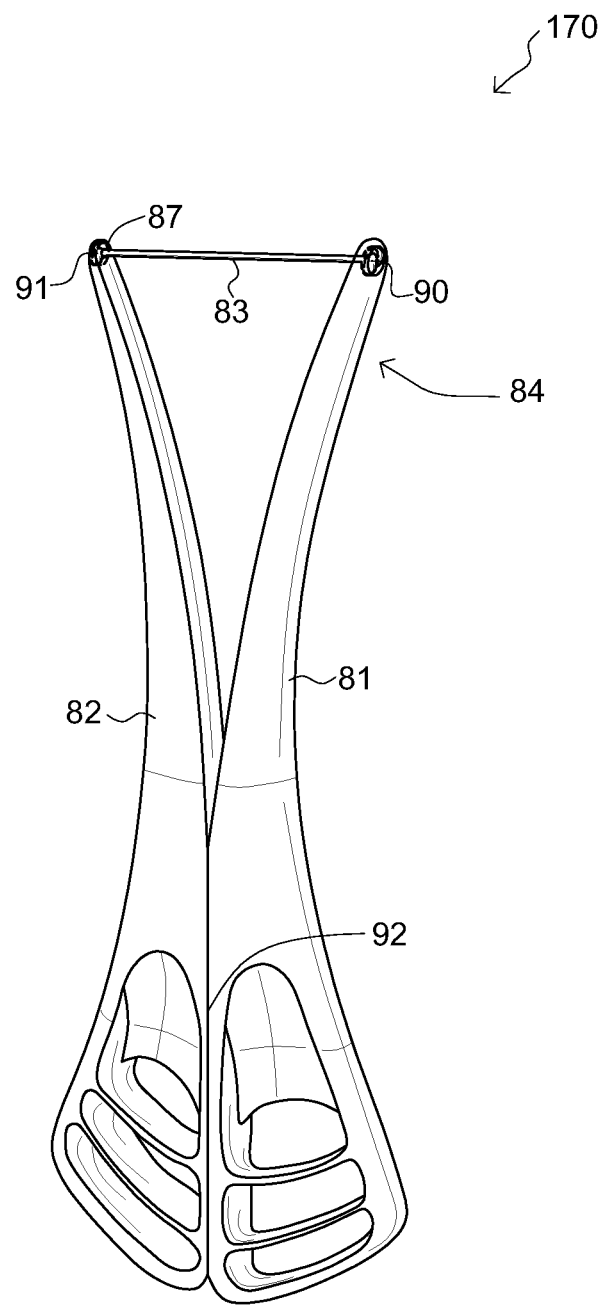
FIG. 20 is a perspective view of a flossing device, according to one embodiment of the invention.

FIG. 20 is a perspective view of a flossing device, according to one embodiment of the invention. There is shown a flossing device 170 including a first elongated member 81 and a second elongated member 82.

The illustrated flossing device 170 includes a first elongated member 81, wherein the first elongated member 81 includes a top region 84. The first elongated member 81 includes an aperture 87 through the top region 84. The aperture 87 is configured to enable a floss member 83 to pass therethrough but not completely.

The illustrated flossing device 170 includes a second elongated member 82 removably coupled to the first elongated member 81. The flossing device 170 includes a floss member 83 coupled to the second elongated member 82 and extending through the aperture 87 of the first elongated member 81. The floss member 83 includes a first enlarged stop member 90 at an end distal from the second elongated member 82 and sized to fit within the aperture 87 but not completely therethrough.

The illustrated second elongated member 82 includes a top. The second elongated member 82 includes an aperture 87 through the top region 84, wherein the floss member 83 includes a second enlarged stop member 91 distal the first stop member 90 and sized to fit within the aperture 87 but not completely therethrough.

The illustrated first enlarged stop member 90 is larger in cross-sectional area than the aperture 87. The first enlarged stop member 90 consists of a deformable material, and is sized sufficiently small to be wedged into the enlarged channel 89 when pulled thereagainst. The first enlarged stop member 90 consists of knotted floss. The first elongated member 81 and the second elongated member 82 are removably coupled together by a breakaway bridge of material 92 therebetween. The first elongated member 81 and the second elongated member 82 are formed from a single unitary piece of material.

Figure 21:
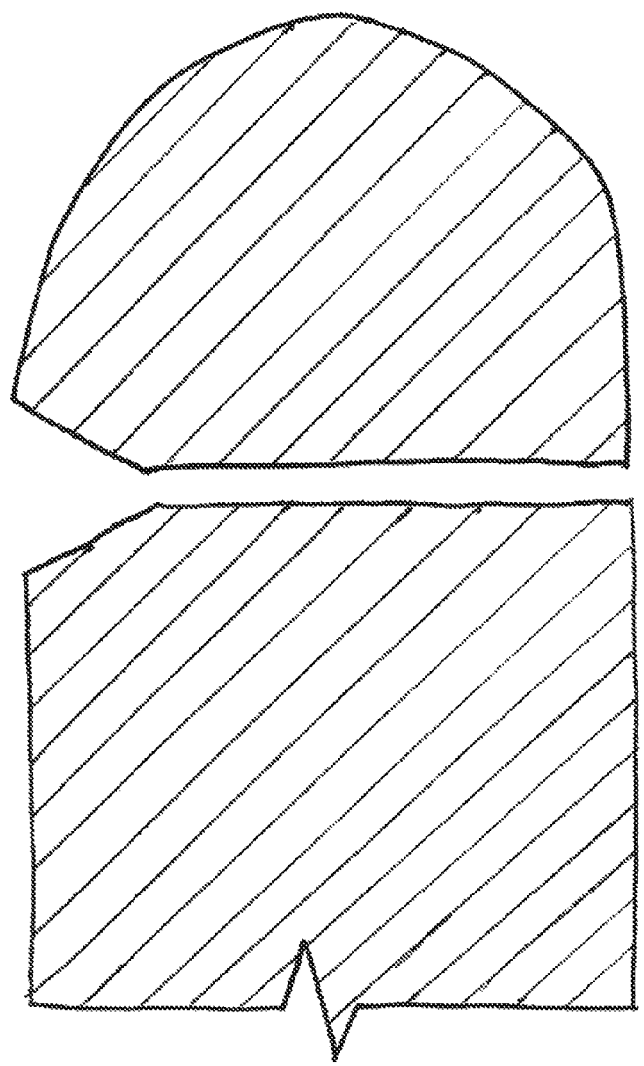
FIG. 21 is a cross-sectional view of a top region, according to one embodiment of the invention.

FIG. 21 is a cross sectional view of a top region according to one embodiment of the invention. There is shown an enlarged channel transitioning into a narrow channel by a gradual decrease in channel width.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the Figures illustrate a pair of elongated members having a square top surface tapering down towards a point, one skilled in the art would appreciate that the first elongated member and the second elongated member may vary in: size, shape, design, configuration, color, length, height, width, curvature, arch, etc., and still perform its intended function.

While the figures illustrate a chopstick-style configuration, it is envisioned that the size of the flossing device may be substantially different than a typical pair of chopsticks. As a non-limiting example, a flossing device may be substantially smaller than a pair of chopsticks, such as but not limited to being sized similarly to other flossing aids.

Additionally, although the figures illustrate a particular retraction mechanism for the floss string, it is envisioned that such mechanisms are plethoric.

It is envisioned that elongated members may be shaped other than straight to facilitate reach, manipulation, and/or handling of the floss.

It is expected that there could be numerous variations of the design of this invention. An example is that the portions described herein may include decorative elements, including but not limited to three-dimensional representations of animals, people, licensed characters and the like.

Finally, it is envisioned that the components of the device may be constructed of a variety of materials, such as but not limited to: plastics, plastic composites, rubber, rubber composites, metals, metal alloys, glass, textiles, etc. and still perform its intended function.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A flossing device, consisting of:
   a first elongated member, having:
      a top region having an exterior side and an interior side opposite each other, the exterior side being on an outside surface of the first elongated member; and
      an aperture through the top region between the exterior side and the interior side, the aperture being countersunk, thereby having a narrow channel coupled to an enlarged channel, the enlarged channel being only on the exterior side of the first elongated member;
   a second elongated member removably coupled to the first elongated member along the interior side of the bottom region of the first elongated member, wherein the exterior side of the first elongated member faces directly away from the second elongated member when the first and second elongated members are coupled together; and
   a floss member coupled to the second elongated member and extending through the aperture of the first elongated member, the floss member including a first enlarged stop member at an end distal from the second elongated member and sized to fit within the enlarged channel but not fit through the narrow channel.

2. The flossing device of claim 1, wherein the second elongated member includes:
   a top region having an exterior side and an interior side opposite each other; and
   an aperture through the top region between the exterior side and the interior side, the aperture being countersunk, thereby having a narrow channel coupled to an enlarged channel, the enlarged channel being on the exterior side of the second elongated member, and wherein the floss member includes a second enlarged stop member distal the first stop member and sized to fit within the enlarged channel of the second elongated member but not fit through the narrow channel of the second elongated member.

3. The flossing device of claim 1, wherein the first enlarged stop member is larger in cross-sectional area than the enlarged channel, consists of a deformable material, and sized sufficiently small to be wedged into the enlarged channel when pulled thereagainst.

4. The flossing device of claim 1, wherein the first enlarged stop member consists of knotted floss.

5. The flossing device of claim 1, wherein the top region of the first elongated member is a column having a cross-section perpendicular to the length thereof that is rectangular.

6. The flossing device of claim 1, wherein the enlarged channel transitions into the narrow channel in a single stepped transition without a gradual decrease in channel width.

7. The flossing device of claim 1, wherein the enlarged channel transitions into the narrow channel by a gradual decrease in channel width.

8. The flossing device of claim 1, wherein the first and second elongated members are formed from a single unitary piece of material.

9. A flossing device, comprising:
   a pair of flossing sticks coupled together by a bridge of breakaway material, of a brittle material such that when pressure is applied thereto a natural break occurs at the breakaway material instead of the surrounding structure, at a bottom region of the pair of flossing sticks, wherein the pair of flossing sticks includes an aperture through a top region of a first floss stick of the pair of floss sticks, extending from an exterior surface of the first floss stick towards a second floss stick of the pair of floss sticks, the aperture being countersunk at the exterior surface and the exterior surface of the first floss stick being a surface that is facing directly away from the second floss stick while the sticks are coupled together; and
   a floss string coupled to a second floss stick, disposed through the aperture and extending out of an exterior surface of the pair of floss sticks, wherein the floss string includes a stop member sized to mate with the countersunk aperture when pulled thereagainst but to not pass through the countersunk aperture, thereby coupling the pair of sticks together with floss therebetween when the pair of flossing sticks are separated at the bridge of breakaway material.

10. The flossing device of claim 9, wherein the second floss stick includes a countersunk aperture in communication with and opposite to the aperture of the first floss stick.

11. The flossing device of claim 10, wherein the pair of flossing sticks and bridge are a singular formed material.

12. The flossing device of claim 11, wherein the stop member is elastic and sized to wedge within the countersunk aperture of the second floss stick such that, when tension is released from the pair of floss sticks when they are separated after having been pulled apart and the stop member so wedged, the stop member remains wedged within the countersunk aperture.

13. The flossing device of claim 12, wherein the floss string includes a second stop member extending out of the countersunk aperture of the second floss stick.

14. A method of manufacturing a flossing device, including the steps of:
   providing a pair of flossing sticks coupled together by a bridge of breakaway material, of a brittle material such that when pressure is applied thereto a natural break occurs at the breakaway material instead of the surrounding structure, at a bottom region of the pair of flossing sticks, wherein the pair of flossing sticks includes an aperture through a top region of a first floss stick of the pair of floss sticks, extending from an exterior surface of the first floss stick towards a second floss stick of the pair of floss sticks, the aperture being countersunk at the exterior surface and the exterior surface of the first floss stick being a surface that is facing directly away from the second floss stick while the sticks are coupled together; and
   threading a floss string through the countersunk hole of each of the joined sticks;
   coupling the floss string to the second stick; and
   providing a stop member at an end of the floss string, the stop member configured to mate with the countersunk hole of the first stick when pulled thereagainst but not to pass therethrough, such that the floss string is coupled to the second floss stick, disposed through the aperture and extending out of an exterior surface of the pair of floss sticks, wherein the floss string includes a stop member sized to mate with the countersunk aperture when pulled thereagainst but to not pass through the countersunk aperture, thereby coupling the pair of sticks together with floss therebetween when the pair of flossing sticks are separated at the bridge of breakaway material.

15. The method of claim 14, wherein the step of coupling the floss string to the second stick includes providing a second stop member at an opposite end of the floss string.

16. The method of claim 14, wherein the step of providing a stop member consists essentially of knotting the floss string.

17. The method of claim 14, wherein the joined sticks are shaped like chopsticks.

18. The method of claim 14, wherein the step of providing a pair of joined sticks includes forming the pair of joined sticks from a single material.

\* \* \* \* \*